(12) United States Patent
Goldshleger et al.

(10) Patent No.: US 9,023,016 B2
(45) Date of Patent: May 5, 2015

(54) IMAGE PROCESSOR FOR INTRA-SURGICAL OPTICAL COHERENCE TOMOGRAPHIC IMAGING OF LASER CATARACT PROCEDURES

(75) Inventors: Ilya Goldshleger, Irvine, CA (US); Guy Holland, San Clemente, CA (US); Adam Juhasz, Costa Mesa, CA (US); Ronald M. Kurtz, Irvine, CA (US); Kostadin Vardin, Aliso Viejo, CA (US)

(73) Assignee: Alcon LenSx, Inc., Aliso Vieojo, CA (US)

( * ) Notice: Subject to any disclaimer, the term of this patent is extended or adjusted under 35 U.S.C. 154(b) by 181 days.

(21) Appl. No.: 13/329,813

(22) Filed: Dec. 19, 2011

(65) Prior Publication Data
US 2013/0158531 A1    Jun. 20, 2013

Related U.S. Application Data

(63) Continuation-in-part of application No. 13/329,529, filed on Dec. 19, 2011.

(51) Int. Cl.
*A61B 5/06* (2006.01)
*A61F 9/008* (2006.01)
*A61B 3/10* (2006.01)

(52) U.S. Cl.
CPC .............. *A61F 9/00825* (2013.01); *A61B 3/102* (2013.01); *A61F 2009/00851* (2013.01); *A61F 2009/0087* (2013.01); *A61F 2009/00887* (2013.01); *A61F 2009/00897* (2013.01)

(58) Field of Classification Search
USPC ................................. 606/2; 607/88
See application file for complete search history.

(56) References Cited

U.S. PATENT DOCUMENTS

| | | | |
|---|---|---|---|
| 4,164,222 A | 8/1979 | Prokhorov et al. |
| 4,198,143 A | 4/1980 | Karasawa |
| 4,235,529 A | 11/1980 | Kawase et al. |

(Continued)

FOREIGN PATENT DOCUMENTS

| | | |
|---|---|---|
| EP | 1444946 | 8/2004 |
| EP | 2322083 | 5/2011 |

(Continued)

OTHER PUBLICATIONS

Aslyo-Vogel et al., "Darstellung von LTK-Läsionen durch optische Kurzkohärenztomographie (OCT) und Polarisationsmikroskopie nach Sirius-Rot-Fäbung", Ophthalmologe, pp. 487-491, 7-97.

(Continued)

*Primary Examiner* — Aaron Roane

(57) ABSTRACT

A cataract surgical system includes a laser source to generate a first set of laser pulses; a guiding optic to guide the first set of laser pulses to a cataract target region in an eye; a laser controller to generate an electronic representation of a target scan pattern, and to control the guiding optic to scan the first set of laser pulses according to a portion of the target scan pattern to create a first photo-disrupted region in the cataract target region; and a Spectral Domain Optical Coherence Tomographic (SD-OCT) imaging system to generate an image of a portion of the first photo-disrupted region. The laser controller can generate an electronic representation of a modified scan pattern in relation to the image generated by the SD-OCT imaging system, and control the guiding optic to scan a second set of laser pulses according the modified scan pattern.

24 Claims, 17 Drawing Sheets

(56) References Cited

U.S. PATENT DOCUMENTS

| | | | |
|---|---|---|---|
| 4,465,348 | A | 8/1984 | Lang et al. |
| 4,520,816 | A | 6/1985 | Schachar et al. |
| 4,533,222 | A | 8/1985 | Ishikawa |
| 4,538,608 | A | 9/1985 | L'Esperance, Jr. |
| 4,554,917 | A | 11/1985 | Tagnon |
| 4,638,801 | A | 1/1987 | Daly et al. |
| 4,764,005 | A | 8/1988 | Webb et al. |
| 4,881,808 | A | 11/1989 | Bille et al. |
| 4,901,718 | A | 2/1990 | Bille et al. |
| 4,907,586 | A | 3/1990 | Bille et al. |
| 5,048,946 | A | 9/1991 | Sklar et al. |
| 5,049,147 | A | 9/1991 | Danon |
| 5,054,907 | A | 10/1991 | Sklar et al. |
| 5,098,426 | A | 3/1992 | Sklar et al. |
| 5,112,328 | A | 5/1992 | Taboada et al. |
| 5,139,022 | A | 8/1992 | Lempert |
| 5,246,435 | A | 9/1993 | Bille et al. |
| 5,255,025 | A | 10/1993 | Volk |
| 5,286,964 | A | 2/1994 | Fountain |
| 5,321,501 | A | 6/1994 | Swanson et al. |
| 5,336,215 | A | 8/1994 | Hsueh et al. |
| 5,391,165 | A | 2/1995 | Fountain et al. |
| 5,439,462 | A | 8/1995 | Bille et al. |
| 5,493,109 | A | 2/1996 | Wei et al. |
| 5,549,632 | A | 8/1996 | Lai |
| 5,656,186 | A | 8/1997 | Mouron et al. |
| 5,738,676 | A | 4/1998 | Hammer et al. |
| 5,779,696 | A | 7/1998 | Berry et al. |
| 5,795,295 | A | 8/1998 | Hellmuth et al. |
| 5,936,706 | A | 8/1999 | Takagi |
| 5,954,648 | A | 9/1999 | Van Der Brug |
| 5,954,711 | A | 9/1999 | Ozaki et al. |
| 5,994,690 | A | 11/1999 | Kulkarni et al. |
| 6,004,314 | A | 12/1999 | Wei et al. |
| 6,095,648 | A | 8/2000 | Birngruber et al. |
| 6,099,522 | A | 8/2000 | Knopp et al. |
| 6,137,585 | A | 10/2000 | Hitzenberger et al. |
| 6,254,595 | B1 | 7/2001 | Juhasz et al. |
| 6,288,784 | B1 | 9/2001 | Hitzenberger et al. |
| 6,314,311 | B1 | 11/2001 | Williams et al. |
| 6,317,616 | B1 | 11/2001 | Glossop |
| 6,337,925 | B1 | 1/2002 | Cohen et al. |
| 6,377,349 | B1 | 4/2002 | Fercher |
| 6,379,005 | B1 | 4/2002 | Williams et al. |
| 6,451,009 | B1 | 9/2002 | Dasilva et al. |
| 6,454,761 | B1 | 9/2002 | Freedman |
| 6,497,701 | B2 | 12/2002 | Shimmick et al. |
| 6,529,758 | B2 | 3/2003 | Shahidi |
| 6,579,282 | B2 | 6/2003 | Bille et al. |
| 6,623,476 | B2 | 9/2003 | Juhasz et al. |
| 6,687,010 | B1 | 2/2004 | Horii et al. |
| 6,730,074 | B2 | 5/2004 | Bille et al. |
| 6,741,359 | B2 | 5/2004 | Wei et al. |
| 6,751,033 | B2 | 6/2004 | Goldstein et al. |
| 6,755,819 | B1 | 6/2004 | Waelti |
| 6,763,259 | B1 | 7/2004 | Hauger et al. |
| 6,769,769 | B2 | 8/2004 | Podoleanu et al. |
| 6,775,007 | B2 | 8/2004 | Izatt et al. |
| 6,863,667 | B2 | 3/2005 | Webb et al. |
| 6,887,232 | B2 | 5/2005 | Bille |
| 6,899,707 | B2 | 5/2005 | Scholler et al. |
| 6,932,807 | B1 | 8/2005 | Tomita et al. |
| 6,991,629 | B1 | 1/2006 | Juhasz et al. |
| 7,006,232 | B2 | 2/2006 | Rollins et al. |
| 7,018,376 | B2 | 3/2006 | Webb et al. |
| 7,027,233 | B2 | 4/2006 | Goldstein et al. |
| 7,061,622 | B2 | 6/2006 | Rollins et al. |
| 7,072,045 | B2 | 7/2006 | Chen et al. |
| 7,072,047 | B2 | 7/2006 | Westphal et al. |
| 7,079,254 | B2 | 7/2006 | Kane et al. |
| 7,102,756 | B2 | 9/2006 | Izatt et al. |
| 7,113,818 | B2 | 9/2006 | Podoleanu et al. |
| 7,126,693 | B2 | 10/2006 | Everett et al. |
| 7,130,054 | B2 | 10/2006 | Ostrovsky et al. |
| 7,133,137 | B2 | 11/2006 | Shimmick |
| 7,139,077 | B2 | 11/2006 | Podoleanu et al. |
| 7,145,661 | B2 | 12/2006 | Hitzenberger |
| 7,148,970 | B2 | 12/2006 | de Boer |
| 7,184,148 | B2 | 2/2007 | Alphonse |
| 7,207,983 | B2 | 4/2007 | Hahn et al. |
| 7,248,371 | B2 | 7/2007 | Chan et al. |
| 7,268,885 | B2 | 9/2007 | Chan et al. |
| 7,280,221 | B2 | 10/2007 | Wei |
| 7,307,733 | B2 | 12/2007 | Chan et al. |
| 7,310,150 | B2 | 12/2007 | Guillermo et al. |
| 7,312,876 | B2 | 12/2007 | Chan et al. |
| 7,319,566 | B2 | 1/2008 | Prince et al. |
| 7,329,002 | B2 | 2/2008 | Nakanishi |
| 7,330,270 | B2 | 2/2008 | O'Hara et al. |
| 7,330,273 | B2 | 2/2008 | Podoleanu et al. |
| 7,335,223 | B2 | 2/2008 | Obrebski |
| 7,336,366 | B2 | 2/2008 | Choma et al. |
| 7,342,659 | B2 | 3/2008 | Horn et al. |
| 7,347,548 | B2 | 3/2008 | Huang et al. |
| 7,352,444 | B1 | 4/2008 | Seams et al. |
| 7,355,716 | B2 | 4/2008 | de Boer et al. |
| 7,364,296 | B2 | 4/2008 | Miller et al. |
| 7,365,856 | B2 | 4/2008 | Everett et al. |
| 7,365,859 | B2 | 4/2008 | Yun et al. |
| 7,370,966 | B2 | 5/2008 | Fukuma et al. |
| 7,371,230 | B2 | 5/2008 | Webb et al. |
| 7,372,578 | B2 | 5/2008 | Akiba et al. |
| 7,388,672 | B2 | 6/2008 | Zhou et al. |
| 7,390,089 | B2 | 6/2008 | Loesel et al. |
| 7,400,410 | B2 | 7/2008 | Baker et al. |
| 7,402,159 | B2 | 7/2008 | Loesel et al. |
| 7,426,037 | B2 | 9/2008 | Ostrovsky et al. |
| 7,433,046 | B2 | 10/2008 | Everett et al. |
| 7,452,077 | B2 | 11/2008 | Meyer et al. |
| 7,452,080 | B2 | 11/2008 | Wiltberger et al. |
| 7,461,658 | B2 | 12/2008 | Jones et al. |
| 7,466,423 | B2 | 12/2008 | Podoleanu et al. |
| 7,470,025 | B2 | 12/2008 | Iwanaga |
| 7,477,764 | B2 | 1/2009 | Haisch |
| 7,480,058 | B2 | 1/2009 | Zhao et al. |
| 7,480,059 | B2 | 1/2009 | Zhou et al. |
| 7,488,070 | B2 | 2/2009 | Hauger et al. |
| 7,488,930 | B2 | 2/2009 | Ajgaonkar et al. |
| 7,492,466 | B2 | 2/2009 | Chan et al. |
| 7,503,916 | B2 | 3/2009 | Shimmick |
| 7,508,525 | B2 | 3/2009 | Zhou et al. |
| 7,535,577 | B2 | 5/2009 | Podoleanu et al. |
| 7,537,591 | B2 | 5/2009 | Feige et al. |
| 7,557,928 | B2 | 7/2009 | Ueno |
| 7,575,322 | B2 | 8/2009 | Somani |
| 7,593,559 | B2 | 9/2009 | Toth et al. |
| 7,602,500 | B2 | 10/2009 | Izatt et al. |
| 7,604,351 | B2 | 10/2009 | Fukuma et al. |
| 7,614,744 | B2 | 11/2009 | Abe |
| 7,630,083 | B2 | 12/2009 | de Boer et al. |
| 7,631,970 | B2 | 12/2009 | Wei |
| 7,633,627 | B2 | 12/2009 | Choma et al. |
| 7,643,152 | B2 | 1/2010 | de Boer et al. |
| 7,797,119 | B2 | 9/2010 | De Boer et al. |
| 7,813,644 | B2 | 10/2010 | Chen et al. |
| 7,898,712 | B2 | 3/2011 | Adams et al. |
| 8,262,646 | B2 | 9/2012 | Frey et al. |
| 8,394,084 | B2 | 3/2013 | Palankar et al. |
| 2001/0022648 | A1 | 9/2001 | Lai |
| 2002/0013574 | A1 | 1/2002 | Elbrecht et al. |
| 2002/0082466 | A1 | 6/2002 | Han |
| 2002/0097374 | A1 | 7/2002 | Payne et al. |
| 2002/0133145 | A1 | 9/2002 | Gerlach et al. |
| 2002/0198516 | A1 | 12/2002 | Knopp |
| 2003/0090674 | A1 | 5/2003 | Zeylikovich et al. |
| 2003/0206272 | A1 | 11/2003 | Cornsweet et al. |
| 2004/0039378 | A1 | 2/2004 | Lin |
| 2004/0059321 | A1 | 3/2004 | Knopp et al. |
| 2004/0151466 | A1 | 8/2004 | Crossman-Bosworth et al. |
| 2004/0243233 | A1 | 12/2004 | Phillips |
| 2005/0010109 | A1 | 1/2005 | Faul |
| 2005/0015120 | A1 | 1/2005 | Seibel et al. |
| 2005/0021011 | A1 | 1/2005 | LaHaye |
| 2005/0173817 | A1 | 8/2005 | Fauver et al. |

(56) References Cited

U.S. PATENT DOCUMENTS

| | | |
|---|---|---|
| 2005/0192562 A1 | 9/2005 | Loesel et al. |
| 2005/0201633 A1 | 9/2005 | Moon et al. |
| 2005/0203492 A1 | 9/2005 | Nguyen et al. |
| 2005/0215986 A1 | 9/2005 | Chernyak et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0077346 A1 | 4/2006 | Matsumoto |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0195076 A1 | 8/2006 | Blumenkranz et al. |
| 2006/0206102 A1 | 9/2006 | Shimmick |
| 2007/0013867 A1 | 1/2007 | Ichikawa |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173791 A1 | 7/2007 | Raksi |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0282313 A1 | 12/2007 | Huang et al. |
| 2007/0291277 A1* | 12/2007 | Everett et al. .................. 356/497 |
| 2007/0299429 A1 | 12/2007 | Amano |
| 2008/0033406 A1 | 2/2008 | Andersen et al. |
| 2008/0049188 A1 | 2/2008 | Wiltberger et al. |
| 2008/0055543 A1 | 3/2008 | Meyer et al. |
| 2008/0056610 A1 | 3/2008 | Kanda |
| 2008/0071254 A1 | 3/2008 | Lummis et al. |
| 2008/0088795 A1 | 4/2008 | Goldstein et al. |
| 2008/0100612 A1 | 5/2008 | Dastmalchi et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0088734 A1 | 4/2009 | Mordaunt |
| 2009/0125005 A1 | 5/2009 | Chernyak et al. |
| 2009/0131921 A1 | 5/2009 | Kurtz et al. |
| 2009/0149742 A1 | 6/2009 | Kato et al. |
| 2009/0157062 A1 | 6/2009 | Hauger et al. |
| 2009/0161827 A1 | 6/2009 | Gertner et al. |
| 2009/0168017 A1 | 7/2009 | O'Hara et al. |
| 2009/0177189 A1* | 7/2009 | Raksi ................................ 606/4 |
| 2009/0268161 A1 | 10/2009 | Hart et al. |
| 2009/0279098 A1* | 11/2009 | Ohbayashi et al. ............ 356/478 |
| 2010/0004641 A1 | 1/2010 | Frey et al. |
| 2010/0004643 A1 | 1/2010 | Frey et al. |
| 2010/0007848 A1 | 1/2010 | Murata |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |
| 2010/0324543 A1 | 12/2010 | Kurtz et al. |
| 2011/0022036 A1 | 1/2011 | Frey et al. |
| 2011/0032533 A1* | 2/2011 | Izatt et al. ...................... 356/497 |
| 2011/0118609 A1 | 5/2011 | Goldshleger et al. |
| 2011/0176716 A1* | 7/2011 | Kim et al. ...................... 382/131 |
| 2011/0196350 A1 | 8/2011 | Friedman et al. |
| 2011/0202044 A1 | 8/2011 | Goldshleger et al. |
| 2011/0222020 A1 | 9/2011 | Izatt et al. |
| 2011/0319873 A1 | 12/2011 | Raksi et al. |
| 2012/0274903 A1 | 11/2012 | Sayeram et al. |

FOREIGN PATENT DOCUMENTS

| | | |
|---|---|---|
| JP | 4-503913 | 7/1992 |
| JP | 2002345758 | 12/2002 |
| JP | 2004-531344 | 10/2004 |
| JP | 2009-523556 | 6/2009 |
| WO | 90/09141 | 7/1992 |
| WO | 98/08048 | 2/1998 |
| WO | 03/002008 | 1/2003 |
| WO | 03/062802 | 7/2003 |
| WO | 2006/074469 | 7/2006 |
| WO | 2007/084694 | 7/2007 |
| WO | 2007106326 | 9/2007 |
| WO | 2007/130411 | 11/2007 |
| WO | 2010/075571 | 7/2010 |

OTHER PUBLICATIONS

Bagayev et al., "Optical coherence tomography for in situ monitoring of laser corneal ablation", Journal of Biomedical Optics, 7(4), pp. 633-642 (Oct. 2002).

Blaha et al., "The slit lamp and the laser in ophthalmology—a new laser slit lamp", SPIE Optical Instrumentation for Biomedical Laser Applications, vol. 658, pp. 38-42, 1986.

Boppart, S., et al., "Intraoperative Assessment of Microsurgery with Three-dimensional Optical Coherence Tomography", Radiology, 208(1):81-86, Jul. 1998.

Davidson, "Analytic Waveguide Solutions and the Coherence Probe Microscope", Microelectronic Engineering, 13, pp. 523-526, 1991.

Drexler, W., et al., "Measurement of the thickness of fundus layers by partial coherence tomography", Optical Engineering, 34(3):701-710, Mar. 1995.

Dyer, P., et al., "Optical Fibre Delivery and Tissue Ablation Studies using a Pulsed Hydrogen Fluoride Laser", Lasers in Medical Science, 7:331-340, 1992.

Fercher et al., "In Vivo Optical Coherence Tomography", American Journal of Ophthalmology, 116(1), pp. 113-114, 1993.

Fujimoto, J., et al., :Biomedical Imaging using Optical Coherent Tomography, 1994, 67.

Hammer, D., "Ultrashort pulse laser induced bubble creation thresholds in ocular media", SPIE, 2391:30-40, 1995.

Hauger, C., et al., "High speed low coherence interferometer for optical coherence tomography", Proceedings of SPIE, 4619:1-9, 2002.

Hee, M., et al., "Optical Coherence tomography of the Human Retina", Arch Ophthalmol, 113:325-332; Mar. 1995.

Hitzenberger et al., "Interferometric Measurement of Corneal Thickness With Micrometer Precision", American Journal of Ophthalmology, 118:468-476, Oct. 1994.

Hitzenberger, C., et al., "Retinal layers located with a precision of 5 μm by partial coherence interferometry", SPIE, 2393:176-181, 1995.

Itoh et al., "Absolute measurements of 3-D shape using white-light interferometer", SPIE Interferometry: Techniques and Analysis, 1755:24-28, 1992.

Izatt et al., "Ophthalmic Diagnostics using Optical Coherence Tomography", SPIE Ophthalmic Technologies, 1877:136-144, 1993.

Izatt, J., et al., "Micrometer-Scale Resolution Imaging of the Anterior Eye In vivo With Optical Coherence Tomography", Arch Ophthalmol, 112:1584-1589, Dec. 1994.

Jean, B., et al., "Topography assisted photoablation", SPIE, vol. 3591:202-208, 1999.

Kamensky, V., et al., "In Situ Monitoring of Laser Modification Process in Human Cataractous Lens and Porcine Cornea Using Coherence Tomography", Journal of biomedical Optics, 4(1), 137-143, Jan. 1999.

Lee et al., "Profilometry with a coherence scanning microscope", Applied Optics, 29(26), 3784-3788, Sep. 10, 1990.

Lubatschowski, "The German Ministry of Research and education funded this OCT guided fs laser surgery in Sep. 2005", http://www.laser-zentrum-hannover.de/download/pdf/taetigkeitsbericht2005.pdf.

Massow, O., et al., "Femtosecond laser microsurgery system controlled by OCT", Laser Zentrum Hannover e.V., The German Ministry of education and research,19 slides, 2007.

(56) References Cited

OTHER PUBLICATIONS

Puliafito, Carmen, "Final technical Report: Air Force Grant #F49620-93-I-03337(1)" dated Feb. 12, 1997, 9 pages.
Ren, Q., et al., "Axicon: A New Laser Beam Delivery System for Corneal Surgery", IEEE Journal of Quantum Electronics, 26(12):2305-2308, Dec. 1990.
Ren, Q., et al., "Cataract Surgery with a Mid-Infrared Endo-laser System", SPIE Ophthalmic Technologies II, 1644:188-192, 1992.
Thompson, K., et al., "Therapeutic and Diagnostic Application of Lasers in Ophthalmology", Proceedings of the IEEE, 80(6):838-860, Jun. 1992.
Thrane, L, et al., "Calculation of the maximum obtainable probing depth of optical coherence tomography in tissue", Proceedings of SPIE, 3915:2-11, 2000.
Wisweh, H., et al., "OCT controlled vocal fold femtosecond laser microsurgery", Laser Zentrum Hannover e.V., The German Ministry of education and research, Grants: 13N8710 and 13N8712; 23 slides, 2008.
PCT International Search Report dated Mar. 21, 2013 for International Application No. PCT/US2012/070435, filed Dec. 19, 2012.
Arimoto et al., "Imaging Properties of Axicon in a Scanning Optical System," Nov. 1, 1992, Applied Optics, 31 (31):6652-6657.
Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27.
Chinn, S.R., et al., "Optical coherence tomography using a frequency-tunable optical source", Optics Letters, 22 (5):340-342, Mar. 1997.
European Search Report, European Patent Application No. 10191057.8, mailed Mar. 16, 2011, to be published by the USPTO.
Fercher et al., "Eye-Length Measurement by Interferometry With Partially Coherent Light," Mar. 1988, Optics Letters, 13(3):186-188.
Fercher et al., "Measurement of Intraocular Distances by Backscattering Spectral Interferometry," May 15, 1995, Optics Comm. 117:43-48.
Hee, M., et al., "Femotosecond transillumination optical coherence tomography", Optics Letters, 18(12):950-952, Jun. 1993.
Huber, R., et al., "Three-dimensional and C-mode OCT imaging with a compact, frequency swept laser source at 1300 nm", Optics Express, 13(26):10523-10538, Dec. 2005.
Izatt et al., "Micron-Resolution Biomedical Imaging With Optical Coherence Tomography," Oct. 1993, Optics & Photonics News, pp. 14-19.
Kamensky, V., et al., "In situ monitoring of the middle IR laser ablation of a cataract-suffered human lens by optical coherent tomography", Proc. SPIE, 2930:222-229, 1996.
Kamensky, V., et al., "Monitoring and animation of laser ablation process in cataracted eye lens using coherence tomography", Proc. SPIE, 2981:94-102, 1997.
Massow, O., et al., "Optical coherence tomography controlled femtosecond laser microsurgery system", Proceedings of the SPIE—Optical Coherence Tomography and Coherence Techniques III, vol. 6627, pp. 662717(1)-662717(6), Aug. 2007.
Ohmi, M., et al., "In-situ Observation of Tissue Laser Ablation Using Optical Coherence Tomography", Optical and Quantum Electronics, 37(13-15):1175-1183, Dec. 2005.
Ostaszewski et al., "Risley prism Beam Pointer", Proc. of SPIE, vol. 6304, 630406-1 thru 630406-10.
PCT International Search Report for International Application No. PCT/US2011/023710 mailed Aug. 24, 2011.
PCT International Search Report for International Application No. PCT/US2011/025332 mailed Sep. 16, 2011.
PCT International Search Report for International Application No. PCT/US2010/056701 mailed Jan. 12, 2011.
PCT International Search Report for International Application No. PCT/US2008/075511 mailed Mar. 12, 2009.
Sarunic, M., et al., "Instantaneous complex conjugate resolved spectral domain and swept-source OCT using 3×3 fiber couplers", Optics Express, 13(3):957-967, Feb. 2005.
Sarunic, M., et al., "Real-time quadrature projection complex conjugate resolved Fourier domain optical coherence tomography", Optics Letters, 31(16):2426-2428, Aug. 2006.
Sarunic, M., et al., "Imaging the Ocular Anterior Segment With Real-Time, Full-Range Fourier-Domain Optical Coherence Tomography", Archives of Ophthalmology, 126(4):537-542, Apr. 2008.
Stern et al., "Femtosecond Optical Ranging of Corneal Incision Depth," Jan. 1989, Investigative Ophthalmology & Visual Science, 30(1):99-104.
Swanson et al., "In vivo retinal imaging by optical coherence tomography", Optics Letters, 18(21), 1864-1866, Nov. 1993.
Tao, Y., et al., "High-speed complex conjugate resolved retinal spectral domain optical coherence tomography using sinusoidal phase modulation", Optics letters, 32(20):2918-2920, Oct. 2007.
Wojtkowski et al., "In Vivo Human Retinal Imaging by Fourier Domain Optical Coherence Tomography," Jul. 2002, Journal of Biomedical Optics 7(3):457-463, 7 pages.
Yun, S.H., et al., "Wavelength-swept fiber laser with frequency shifted feedback and resonantly swept intra-cavity acoustooptic tunable filter", IEEE Journal of Selected Topics in Quantum Electronics, 3(4):1087-1096, Aug. 1997.
PCT International Search Report for International Application No. PCT/US2011/040223 mailed Jun. 13, 2011.
PCT International Search Report corresponding to PCT Application Serial No. PCT/US2011/051466 dated Apr. 10, 2012.
Partial International Search Report corresponding to PCT Application Serial No. PCT/US2012/035927 dated Aug. 3, 2012.

\* cited by examiner

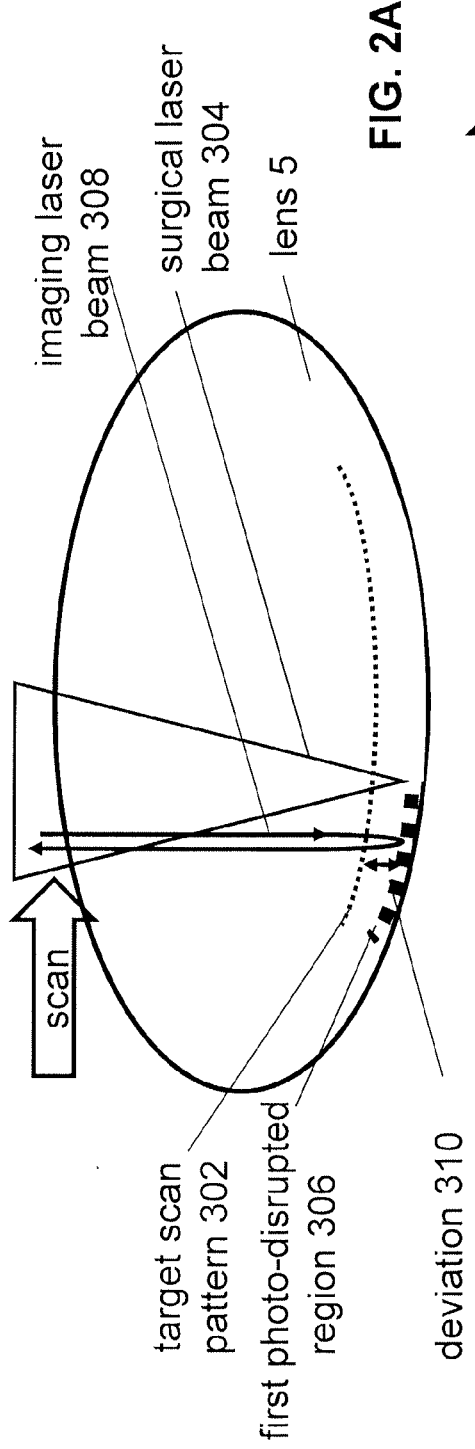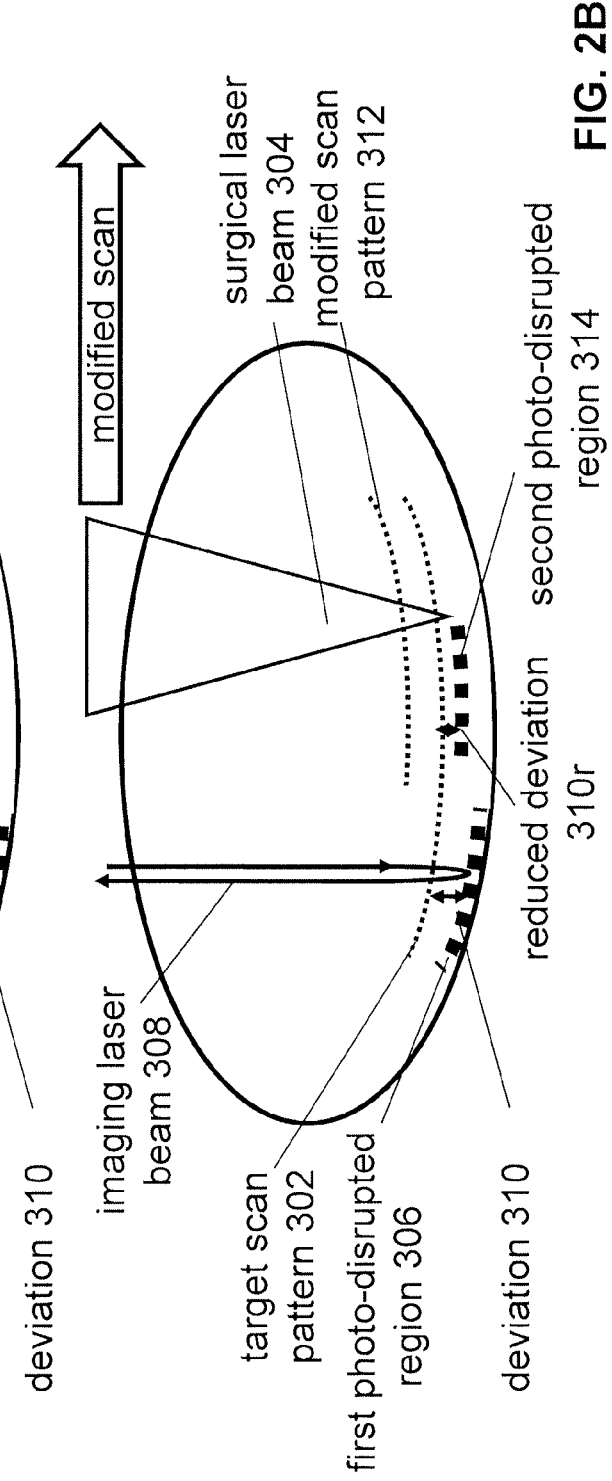

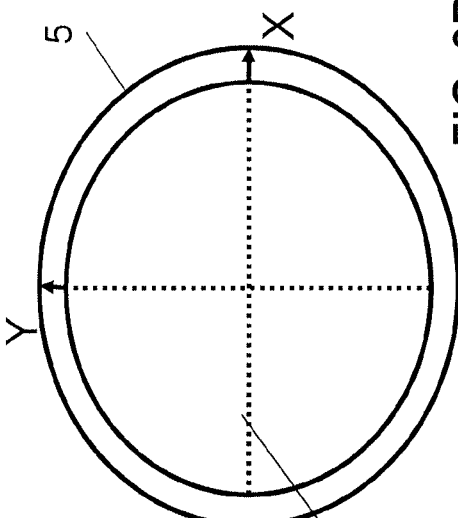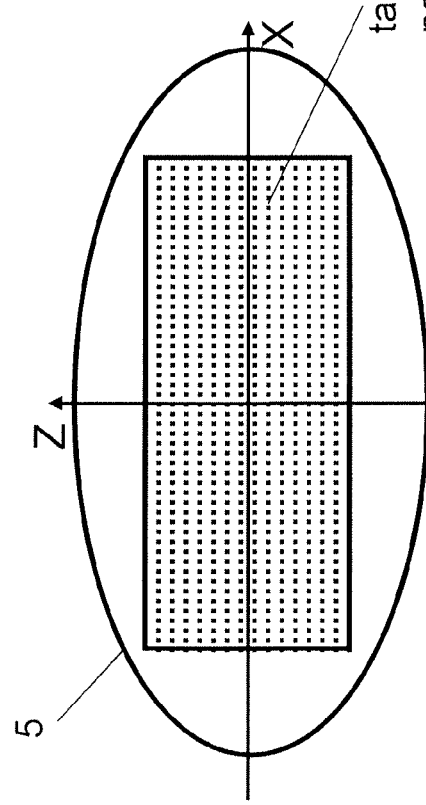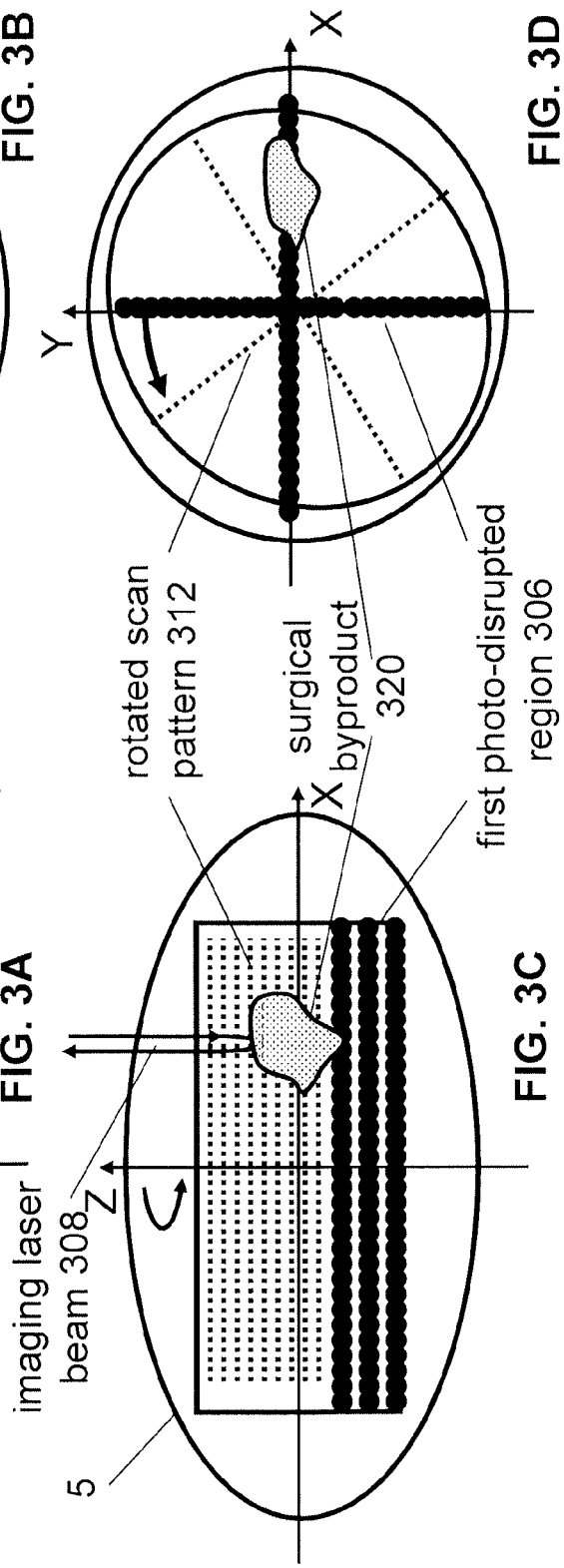

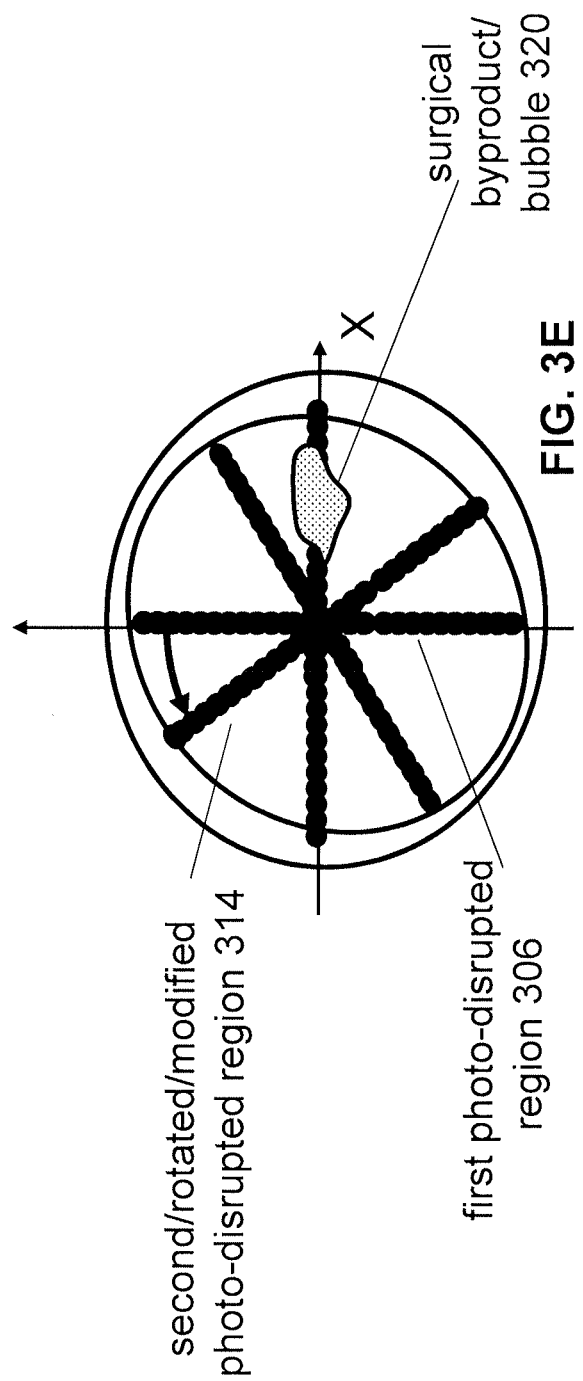

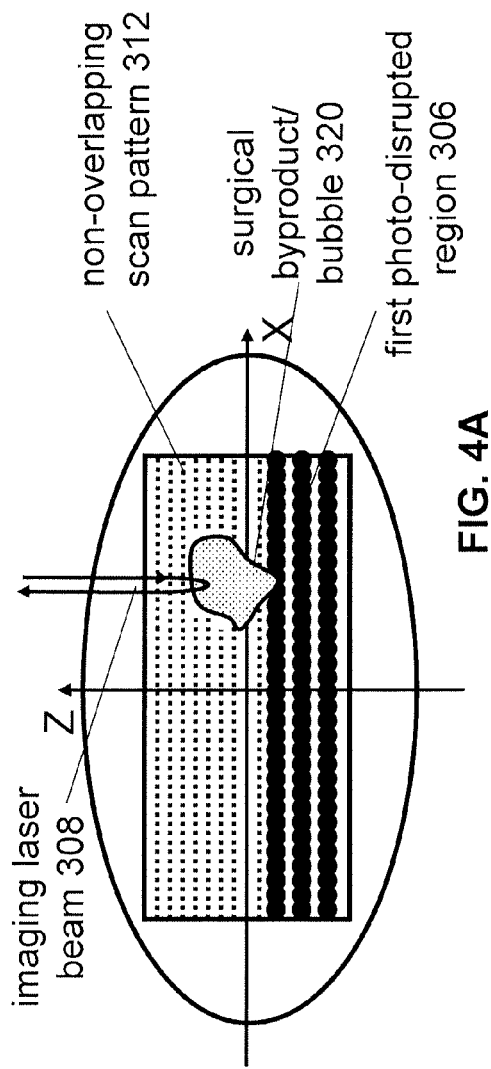
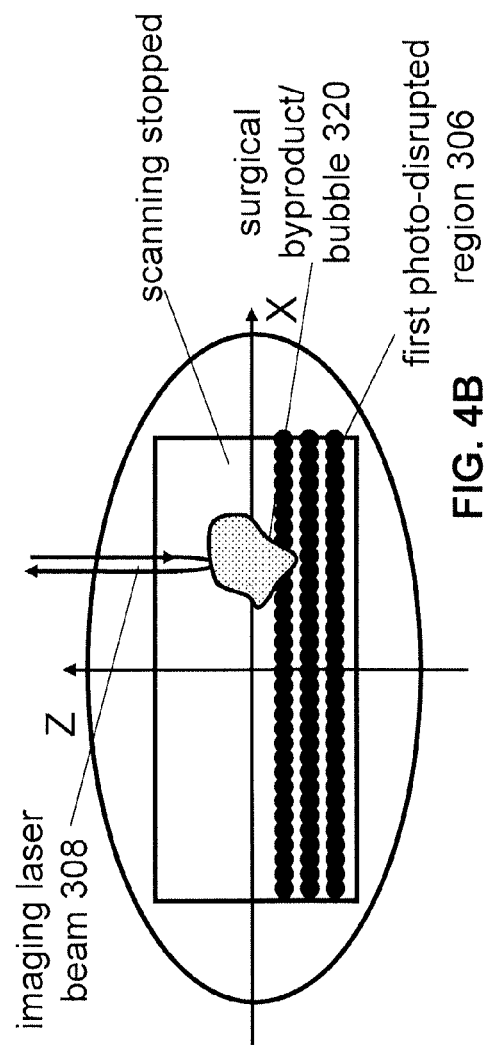
FIG. 4A
FIG. 4B

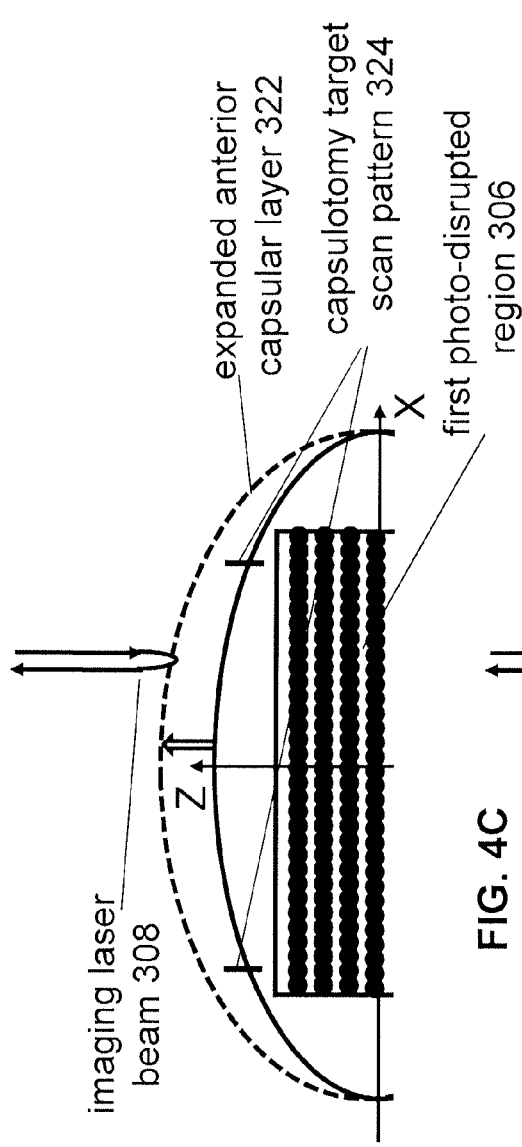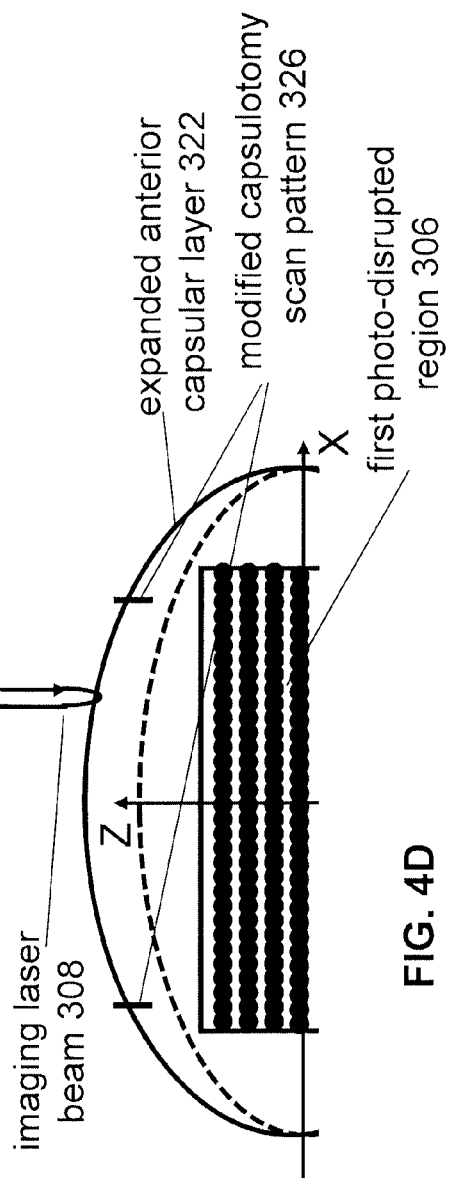
FIG. 4C
FIG. 4D

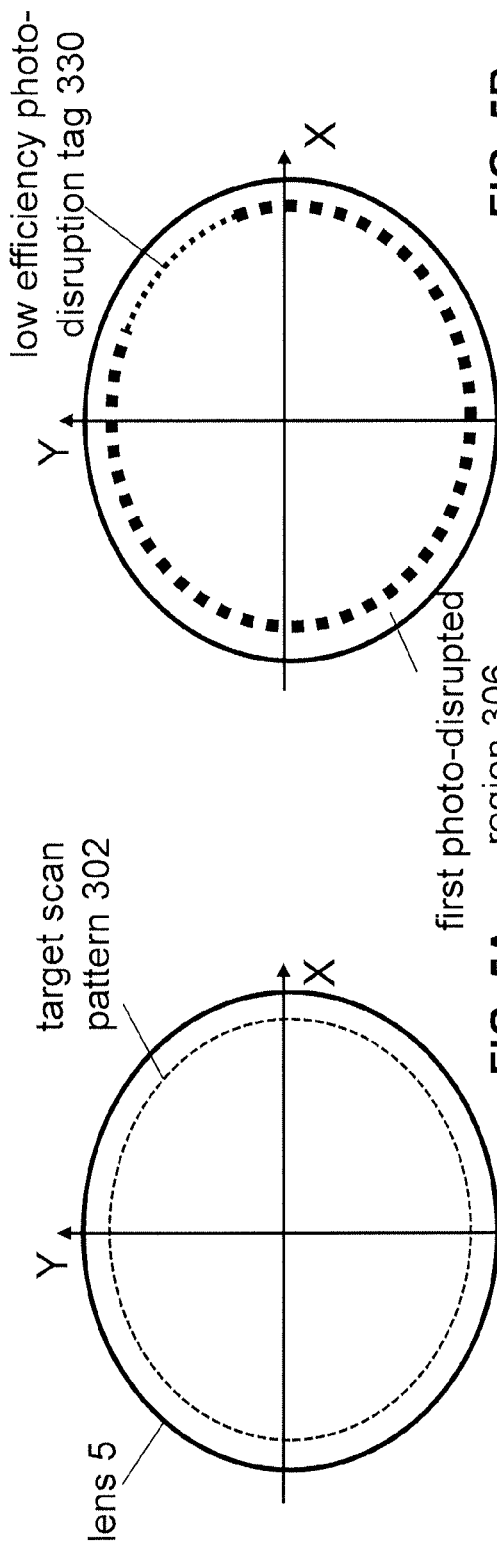
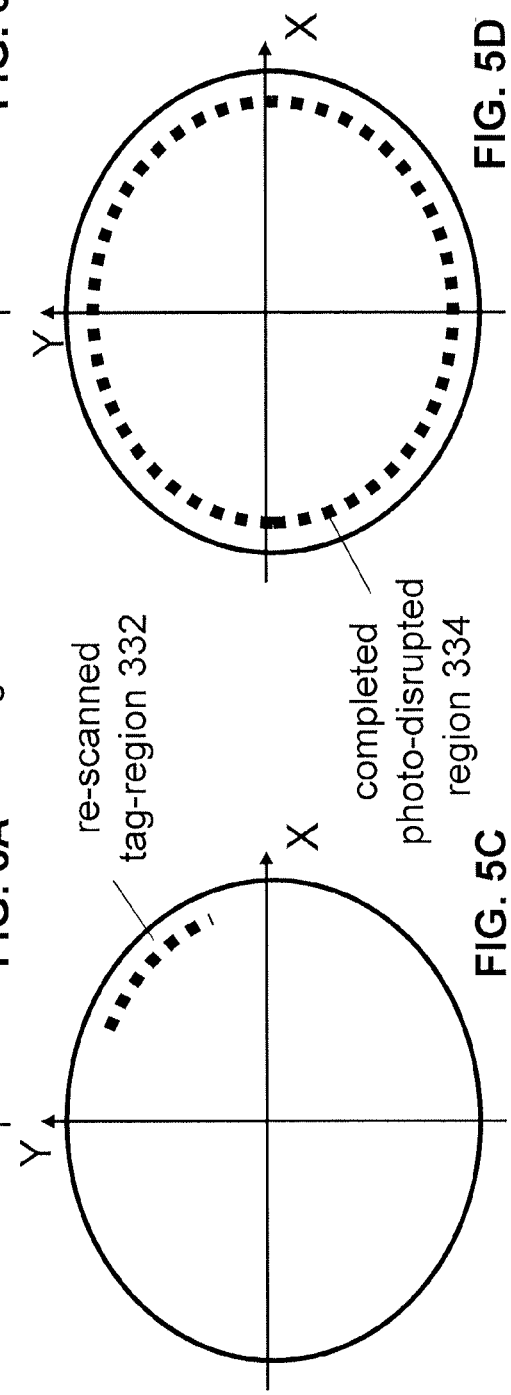
FIG. 5A
FIG. 5B
FIG. 5C
FIG. 5D

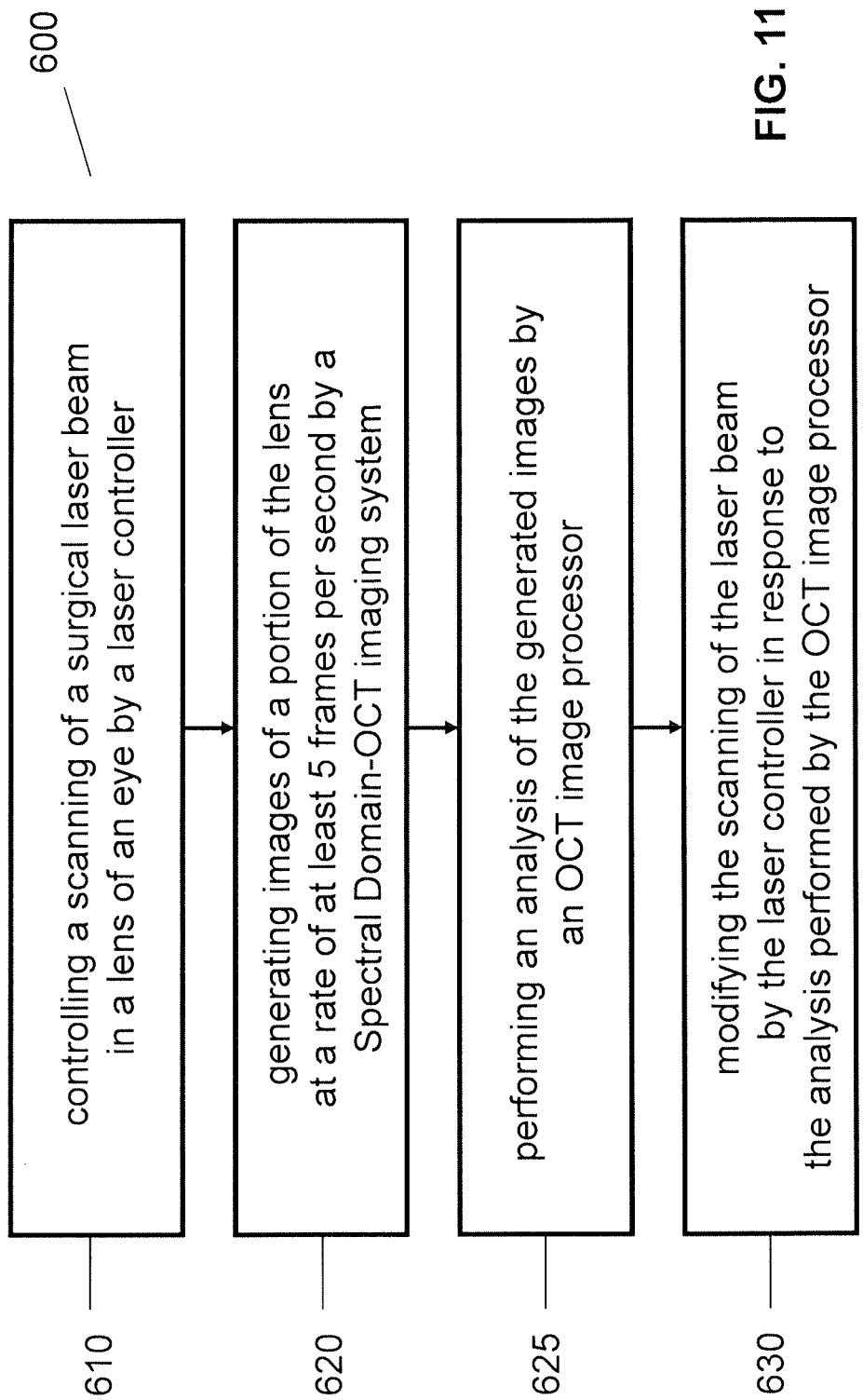

IMAGE PROCESSOR FOR INTRA-SURGICAL OPTICAL COHERENCE TOMOGRAPHIC IMAGING OF LASER CATARACT PROCEDURES

CROSS-REFERENCE TO RELATED APPLICATION

This application is a continuation-in-part of the co-pending application "Intra-surgical Optical Coherence Tomographic Imaging of Cataract Procedures", Ser. No. 13/329,529 filed on Dec. 19, 2011, which application is hereby incorporated in its entirety by reference.

TECHNICAL FIELD

This patent document relates to applying Optical Coherence Tomographic imaging systems during cataract procedures. In more detail, this patent document relates to intra-surgical Spectral Domain Optical Coherence Tomographic imaging of cataract procedures.

BACKGROUND

Cataract surgery is experiencing a revolution. The precision and speed of many aspects of the cataract procedures has improved dramatically in the last few years. Pulsed surgical laser systems with femtosecond laser pulses provide very precisely controlled cutting functionalities. Advanced optical systems provide unprecedented control over the placement and targeting of the laser pulses. In addition, imaging systems provide high quality images to assist the surgeons to plan and execute the cataract surgical procedures. However, there is still lot of room for the improvement of the cataract surgical systems, especially in the area of imaging.

SUMMARY

One area where substantial improvement is possible and called for is providing more extensive and actionable imaging information for the cataract surgeon. The most advanced of today's systems include an Optical Coherence Tomographic (OCT) imaging system. Prior to the cataract surgery, these systems can generate and display an in-depth curvilinear or cross sectional reference image of the anterior segment of the eye that includes the cornea, the anterior chamber and the lens. The surgeon can plan the surgical procedure by placing marks on the displayed reference image to input characteristic points or end-points of the various cuts and regions to be photo-disrupted or photo-treated. An interactive interface of a laser controller can sense these marks and translate them into electronic control signals to guide the surgical laser beam to form the corresponding cuts.

To place the invention in context, it is recalled that a cataract procedure with a surgical laser system can include the following steps. (1) First, the lens can be photo-disrupted inside the capsular bag by scanning the surgical laser beam according to a photo-disruption pattern. Depending on the hardness of the cataract, the disruption pattern, the degree of disruption and the desired surgical outcomes, this process can be referred to as a chop, a fragmentation, or a lysis. (2) Second, a capsular lid or cap can be cut in the capsular bag or anterior capsular layer by a circular capsulotomy, anterior capsulotomy or continuous curvilinear capsulotomy. The capsular lid or cap is formed so that when it is removed, a hole is opened up in the capsular bag through which the surgeon can extract or aspirate the photo-disrupted lens from the capsular bag. (3) An access cut can be formed next in the sclera, limbus, or peripheral corneal region of the eye. Through this access cut surgical devices, such as a forceps or a phaco-tip can be inserted into the eye. (4) Next, the capsular lid or cap can be removed by one of the inserted surgical devices to form the aforementioned capsular opening. (5) Often, the surgical laser does not disrupt the lens completely. In such cases, a phaco-tip can be inserted into the capsular bag to complete the disruption of the lens by applying ultrasound and chopping. (6) Subsequently, the fragments of the lens can be removed or aspirated through the capsular opening. (7) Finally, an intra ocular lens (IOL) can be inserted to restore vision in the eye. The order of steps (1) and (2) can be reversed in some procedures.

Cataract procedures can be complemented by forming additional cuts, such as limbal relaxing incisions or arcuate incisions in the cornea, and various additional access cuts.

However, once the photo-disruption by the surgical laser beam started to form the planned cuts, today's imaging systems do not generate additional images that could provide actionable information or feedback for the cataract surgeon. This is primarily due to the fact that with the modern surgical systems the cataract surgical procedures can last a rather short time, such as 10-20 seconds for a capsulotomy or 30-40 seconds for a lens photo-disruption. Existing imaging systems are unable to image the photo-disrupted region with sufficient resolution in such a short surgical time. Even less are they capable of analyzing the image of the photo-disrupted region to provide actionable feedback, or of actively modifying the ongoing surgical procedure. Such functionalities would require faster imaging performance and additional or different electronic and imaging systems.

While imaging and analyzing the affected regions during the short surgical times is hard, a feedback based on such an imaging or analysis would be highly desirable both to improve the precision of the surgical procedure and to manage unexpected surgical complications. For example, a capsulotomy may not cut through the entire capsular bag at some portions of the circular cutting line so that the circular lid or cap remains attached to the rest of the capsule at these "tags". When subsequently the surgeon attempts to remove the circular lid with a forceps, the capsular bag can be torn at the tags, leading to jagged edges or substantial tears. Had the surgeon been provided with an image of the incomplete capsulotomy in time, he may have opted for re-scanning the capsulotomy circle with the laser to cut through the tags rather than commencing the removal of the partially undetached lid.

In other cases, when the photo-disruption of the lens is performed, the surgical laser may be scanned too close to the posterior capsular layer, possibly puncturing it. Such a puncture may necessitate a complex emergency vitrectomy procedure, substantially elevating the risk of the entire cataract procedure. Again, had the surgeon been provided with an imaging feedback in a timely manner, she could have modified the scanning pattern to guide the surgical laser beam away from the posterior capsular layer, preventing the vitrectomy.

In yet other cases, the surgical laser system may be miscalibrated: the laser controller may have miscalculated the location of the laser pulses for a variety of reasons, including optical aberrations, manufacturing tolerance problems of the laser, a mischaracterization of the refractive properties of the lens, a pre-operative diagnostic error, a movement or shape-change of the eye, and thermal creep of the components. In an example, while the surgeon may have placed the marks on a reference image to form a surgical cut e.g. 100 microns from the posterior capsular layer, the guiding optic may have directed the surgical laser pulses to a location only 50 microns from the posterior capsular layer because of the miscalibration, elevating the risk and reducing the precision and safety of the cataract procedure. As above, had the surgeon been provided with an image of the progress of the surgery, she could have discovered the miscalibration before the photo-disruption got to the dangerously close 50 micron distance from the posterior capsular layer.

In yet another example, the miscalibration can be caused by the entire lens having moved along the optical axis because of a difference of the pressure in the anterior chamber and in the posterior chamber, or vitreous, located behind the lens along the optical beam path. The pressure can change for a variety of reasons after the reference image has been taken, such as because of the pressure exerted by the patient interface. Also, the eye being a dynamical system, the internal pressures in the anterior and posterior chambers can change in time, e.g. as the internal pressures equilibrate with the external pressures over an extended period such as seconds or tens of seconds after the patient interface is docked to the eye.

In yet another example, the miscalibration can be caused by the lens curvature having changed because of accommodation. The accommodation can be caused by the patient before and during the procedure. Surgeons typically administer drugs to arrest or suppress accommodation, in effect expanding the pupil. However, these drugs have different effects on different patients and even these different effects follow different timelines. Again, in the last two examples, as before, had the surgeon been provided by updated or timely images during the procedure, she could have recognized the miscalibration and could have taken preventive or corrective action.

A common feature of these and many other possible surgical complications is that they become detectable only after the photo-disruption of the target tissue has been started. As described above, however, forming an image in an imaging time shorter than a surgical time of 10, 20, 40 or 60 seconds can be a great challenge for today's imaging systems, especially if a high resolution image is necessary to provide actionable imaging information. And it can be prohibitively challenging for the existing systems in addition to analyze the image in order to display a feedback or a suggested corrective action, or in order to actively modify the scanning of the surgical photo-disrupting laser beam.

The present patent document describes embodiments of cataract surgical systems with advanced imaging systems that are configured to image and in some implementations to analyze the regions photo-disrupted by the surgical laser beam in an imaging time shorter than typical surgical times. These embodiments therefore enable the modification of the cataract surgical procedure in real time, either by the surgeon or by the surgical system itself, promising a qualitative improvement of the efficacy and safety of modern cataract surgery.

In particular, in an embodiment a cataract surgical system may include a laser source, configured to generate a first set of laser pulses; a guiding optic, coupled to the laser source, configured to guide the first set of laser pulses to a cataract target region in an eye; a laser controller, configured to generate an electronic representation of a target scan pattern and to control the guiding optic to scan the first set of laser pulses according to a portion of the target scan pattern to create a first photo-disrupted region in the cataract target region; a Spectral Domain Optical Coherence Tomographic (SD-OCT) imaging system, configured to generate an image of a portion of the first photo-disrupted region; and an OCT image processor, configured to perform an image analysis of the image, wherein the laser controller is configured to generate an electronic representation of a modified scan pattern in relation to the image analysis performed by the OCT image processor, and to control the guiding optic to scan a second set of laser pulses according the modified scan pattern to create a second photo-disrupted region. In some embodiments, the imaging system can be a Swept-Source Optical Coherence Tomographic (SS-OCT) imaging system.

In some embodiments, a cataract surgical system can include a surgical laser system, configured to generate a surgical laser beam and to scan the surgical laser beam in a cataract target region; a Spectral Domain Optical Coherence Tomographic (SD-OCT) imaging system, configured to generate an image of a portion of the cataract target region; and an OCT image processor, configured to perform an image analysis of the image, to recognize a surgically undesirable feature in the image, and to generate a control signal to stop or suspend the scanning of the surgical laser beam.

In some embodiments, an ophthalmic surgical method can include generating an electronic representation of a target scan pattern for a lens of an eye by a laser controller; generating and scanning a laser beam in the lens of the eye according to the target scan pattern by a surgical laser system, creating a cut in the lens; generating an image of a portion of the eye and the cut with a Spectral Domain Optical Coherence Tomographic imaging system after the scanning of the laser beam started; performing an image analysis of the generated image with an OCT image processor; generating an electronic representation of a modified scan pattern by the laser controller in relation to the performed image analysis; and generating and scanning the laser beam in the lens of the eye according to the modified scan pattern by the surgical laser system, creating a modified cut.

In some embodiments, a method of cataract surgery can include controlling a scanning of a laser beam in a lens of an eye by a laser controller; generating images of a portion of the lens at a rate of at least 5 frames per second by a Spectral Domain Optical Coherence Tomographic imaging system; performing an analysis of the generated images by an OCT image processor; and modifying the scanning of the laser beam by the laser controller in response to the analysis performed by the OCT image processor.

BRIEF DESCRIPTION OF THE DRAWINGS

FIGS. 2A-C illustrate forming a first and a modified second photo-disrupted region.

FIGS. 3A-E illustrate the modification of scan patterns after a surgical byproduct has been detected.

FIGS. 4A-B illustrate the modification of the scan pattern after a surgical byproduct has been detected.

FIGS. 4C-D illustrate the modification of the capsulotomy scan pattern after the lens capsule expanded.

FIGS. 5A-D illustrate a re-scanning of an inefficient capsulotomy.

FIG. 11 illustrates an imaging-aided cataract surgical method.

DETAILED DESCRIPTION

Implementations and embodiments in this patent document describe cataract surgical systems that generate timely imaging feedback either to assist a surgeon to adjust the surgical procedure based on the feedback, or to determine and carry out such an adjustment by themselves.

Figure 1A:
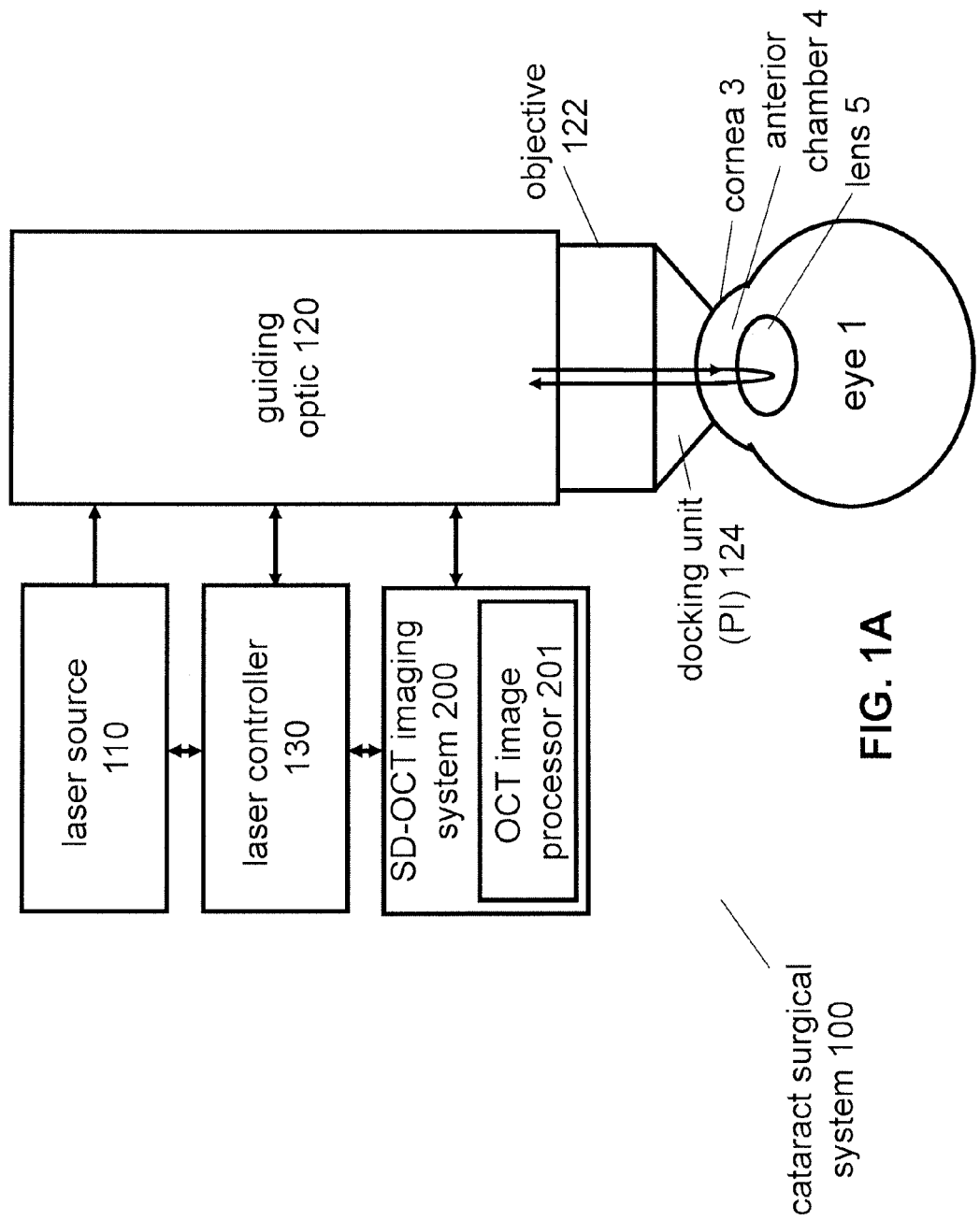
FIG. 1A illustrates an embodiment of a cataract laser surgical system.

FIG. 1A illustrates a cataract surgical system 100, including a laser source 110 to generate a laser beam of a first set of laser pulses. These laser pulses can have a duration or pulse length in the range of 1-1,000 femtoseconds or 1-1,000 picoseconds. The energy and power of the laser beam can be selected to achieve a well controlled photo-disruption in the selected target region efficiently without causing damage in other ophthalmic tissues such as in the photosensitive retina. The cataract surgical system 100 can also include a guiding optic 120, coupled to the laser source 110 to guide the first set of laser pulses through a cornea 3 and an anterior chamber 4 to a lens 5 of an eye 1. The lens 5 is enveloped by a capsular layer or bag 6. The guiding optic 120 can be configured to guide the laser beam into a cataract target region through an objective 122 and a docking unit or patient interface (PI) 124 that can dock onto the eye 1 and immobilize it relative to the cataract surgical system 100 by applying vacuum suction. In some embodiments, there may not be a direct or immobilizing connection between the objective 122 and the eye 1. These embodiments may employ instead eye trackers to correlate the imaging process with possible movements of the eye, for example.

The cataract target region can be located in an anterior segment of the eye 1 that includes the cornea 3, the anterior chamber 4, the lens 5 and the capsular bag 6 of the eye 1. The cataract target region can be, for example, a circle, cylinder, or slanted cylinder in an anterior capsular layer or capsular bag 6 of the lens 5 when a capsulotomy is performed. The cataract target region can also be a large volume fraction of the lens 5 to achieve a photo-disruption, a chop or a lysis of the lens 5 or at least of its nucleus. The cataract target region can also be in the cornea 3, such as an access cut to create a port for the insertion of cataract surgical devices. In more comprehensive cataract procedures, such as in refractive cataract surgery, additional limbal relaxing cuts or incisions (LRI) or arcuate incisions can be formed as well.

The capsulotomy can have a diameter in the 3-6 mm range, as dictated by the design of the intra ocular lens, or IOL, to be inserted into the preserved lens capsule at a z-depth in the 2-4 mm range, where the z-depth is measured along an optical axis of the cataract surgical system 100, using a contact surface of the cornea 3 and the PI 124 as a zero reference level for the z-depth. The target region of a lens photo-disruption can extend from 2-4 mm z-depth to 7-10 mm z-depth, with a diameter of 4-8 mm. Finally, the corneal LRI, arcuate and access cuts can be formed in the 0-2 mm z-depth at the large diameter of 6-14 mm to minimize or altogether avoid directly impacting the field of vision. These numerical ranges show that the challenges of cataract procedures substantially exceed those of the purely corneal procedures—such as LASIK—or retinal procedures. Both corneal/LASIK and retinal procedures are performed in a much narrower z-depth range and in a much smaller overall surgical volume than cataract procedures. Corneal procedures are typically restricted to 0.1-0.5 mm z-depth ranges as the thickness of the cornea rarely exceeds 1 mm and the photo-disruption typically does not cut through the entire cornea to keep the anterior chamber intact. Typical diameters of corneal cuts can be in the 2-3 mm range. While retinal procedures are performed deep in the posterior segment of the eye 1 at a large z-depth, the range of z-depths where the cuts are formed is typically less than 2 mm, the overall thickness of the retinal layers of interest.

In contrast, cataract procedures typically involve the photo-disruption in most or all of the above described cataract target regions, both in the cornea 3 and in the lens 5. Therefore, cataract procedures can involve cuts in a z-depth range of 4 mm or larger, sometimes 6 mm or larger. These cataract z-depth ranges are substantially larger than the above described z-depth ranges of the corneal or retinal procedures. Further, the diameter of the cataract-related cuts also exceeds that of the corneal cuts substantially. Therefore, forming cataract cuts poses substantially harder challenges for the design of a cataract surgical system, including its imaging system, than forming corneal cuts poses for the design of a LASIK system, or forming retinal cuts poses for the design of a retinal surgical system.

The cataract surgical system 100 can also include a laser controller 130 to generate an electronic representation of a target scan pattern and to control the guiding optic 120 to scan the first set of laser pulses according to a portion of the target scan pattern to create a first photo-disrupted region in the cataract target region.

As described above, the cataract target region can be a proximity of an anterior capsular layer and the target scan pattern can be a set of target points on a circle or cylinder in the anterior capsular layer of the lens 5 for a circular capsulotomy, an anterior capsulotomy, or a curvilinear capsulotomy.

Or, the cataract target region can be a portion of the lens 5 and the target scan pattern can be a set of target points on radial chop planes, cylinders, a spiral pattern, or a mesh pattern to induce photo-disruption of the lens 5 itself. The points of the target scan pattern can be defined e.g. by their radial or (x,y,z) coordinates. These coordinates can be electronically represented in a processor, based on executables stored in a corresponding memory of the laser controller 130.

The cataract surgical system can also include a Spectral Domain Optical Coherence Tomographic (SD-OCT) imaging system 200 to generate an image of a portion of the first photo-disrupted region, created by the scanning of the surgical laser beam. The SD-OCT imaging system 200 can be configured to couple an imaging beam into the guiding optic 120 to be guided into the eye 1 and to receive a returned imaging beam from the guiding optic 120. The SD-OCT imaging system 200 can be configured to generate the image or images of the first photo-disrupted region during the surgery to provide timely or actionable feedback for the surgeon or for the laser controller 130, as described below in detail.

Figure 1B:
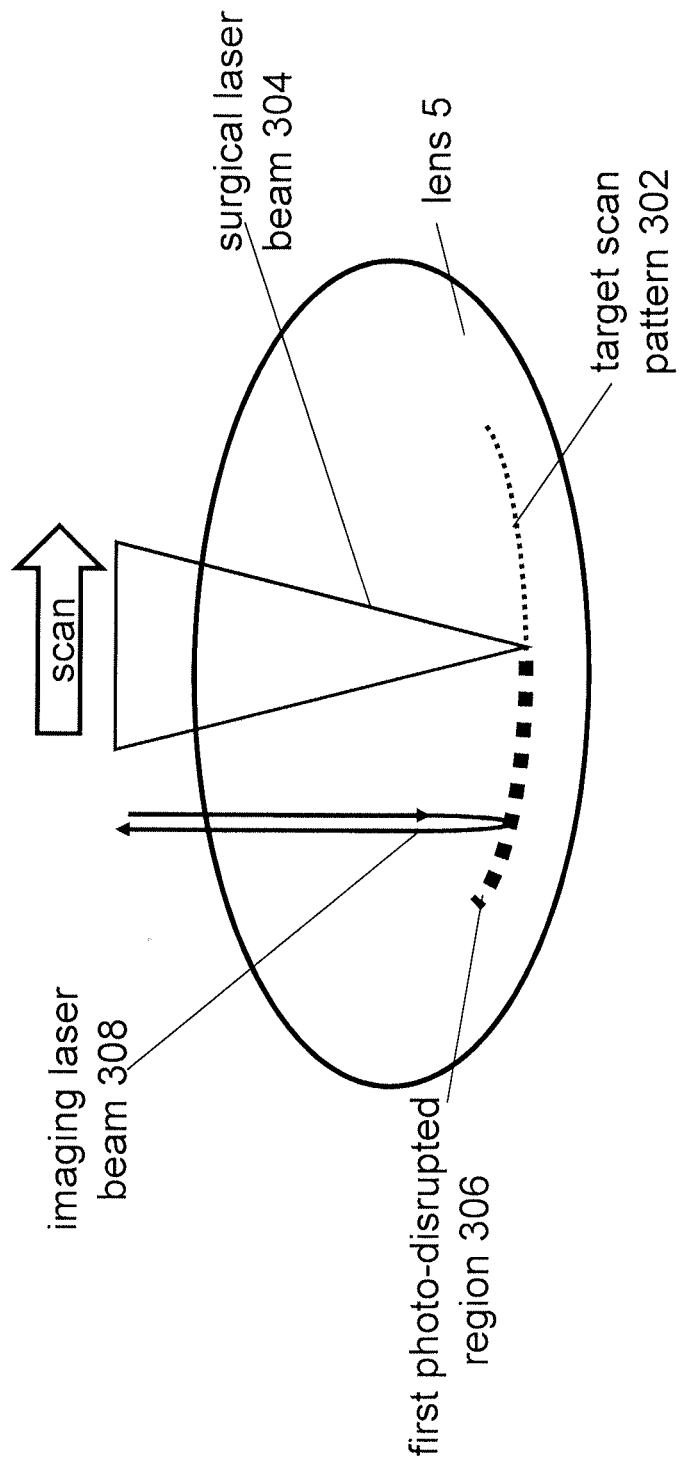
FIG. 1B illustrates an imaging aided photo-disruption in a lens target region.

FIG. 1B illustrates an operation of the cataract surgical system 100. In this example, the laser controller 130 can generate the electronic representation of a target scan pattern 302 in the cataract target region, an arc close to the posterior capsular layer. The guiding optic 120 can focus and scan the first set of laser pulses of a surgical laser beam 304, generated by the laser source 110, through the points of the target scan pattern 302 to create a first photo-disrupted region 306. The first photo-disrupted region 306 in this example can consist of a set of bubbles or cavitation bubbles, formed at the points of the target scan pattern 302. After the photo-disruption started, the SD-OCT imaging system 200 can scan an imaging beam 308 through the cataract target region to generate an image of the first photo-disrupted region 306. In some implementations, the imaging beam 308 and the surgical laser beam 304 can be scanned or guided by the same shared guiding optic 120. In other implementations, only part of the optical pathway can be shared and the imaging beam 308 can be partly scanned by an additional non-shared imaging-guiding optic. All these designs are embodiments of the guiding optic 120.

If the image generated by the SD-OCT imaging system 200 indicates that the procedure is progressing as planned, such as the photo-disrupted bubbles 306 are formed according to the target scan pattern 302 and without unintended consequences, the laser controller 130 can continue scanning the surgical laser beam 304 along the original target scan pattern 302. However, if the image indicates that there is a deviation from the planned procedure, the laser controller 130 can respond by generating an electronic representation of a modified scan pattern and control the guiding optic 120 to scan a second set of laser pulses according the modified scan pattern to create a second photo-disrupted region, as will be illustrated in subsequent figures.

In some embodiments, there may be no direct coupling between the SD-OCT imaging system 200 and the laser controller 130. In these embodiments, the SD-OCT imaging system 200 can display the image of the first photo-disrupted region 306, and a system operator, such as the surgeon can enter modified scan parameters to cause the laser controller 130 to generate the electronic representation of the modified scan pattern.

FIG. 1A illustrates that in some embodiments, the SD-OCT imaging system 200 can include an OCT image processor 201 that can analyze the generated image after the photo-disruption started. In some embodiments, the OCT image processor 201 can display the results of the analysis for the surgeon to provide a timely and actionable feedback during the surgery, so that the surgeon can enter a modified scan pattern into the laser controller 130. In the example of FIG. 1B, the OCT image processor 201 may be configured to measure the distance of the first photo-disrupted region 306 from the posterior capsular layer and if the distance becomes smaller than a preset margin of safety, then display warning signals for the surgeon.

Figure 1C:
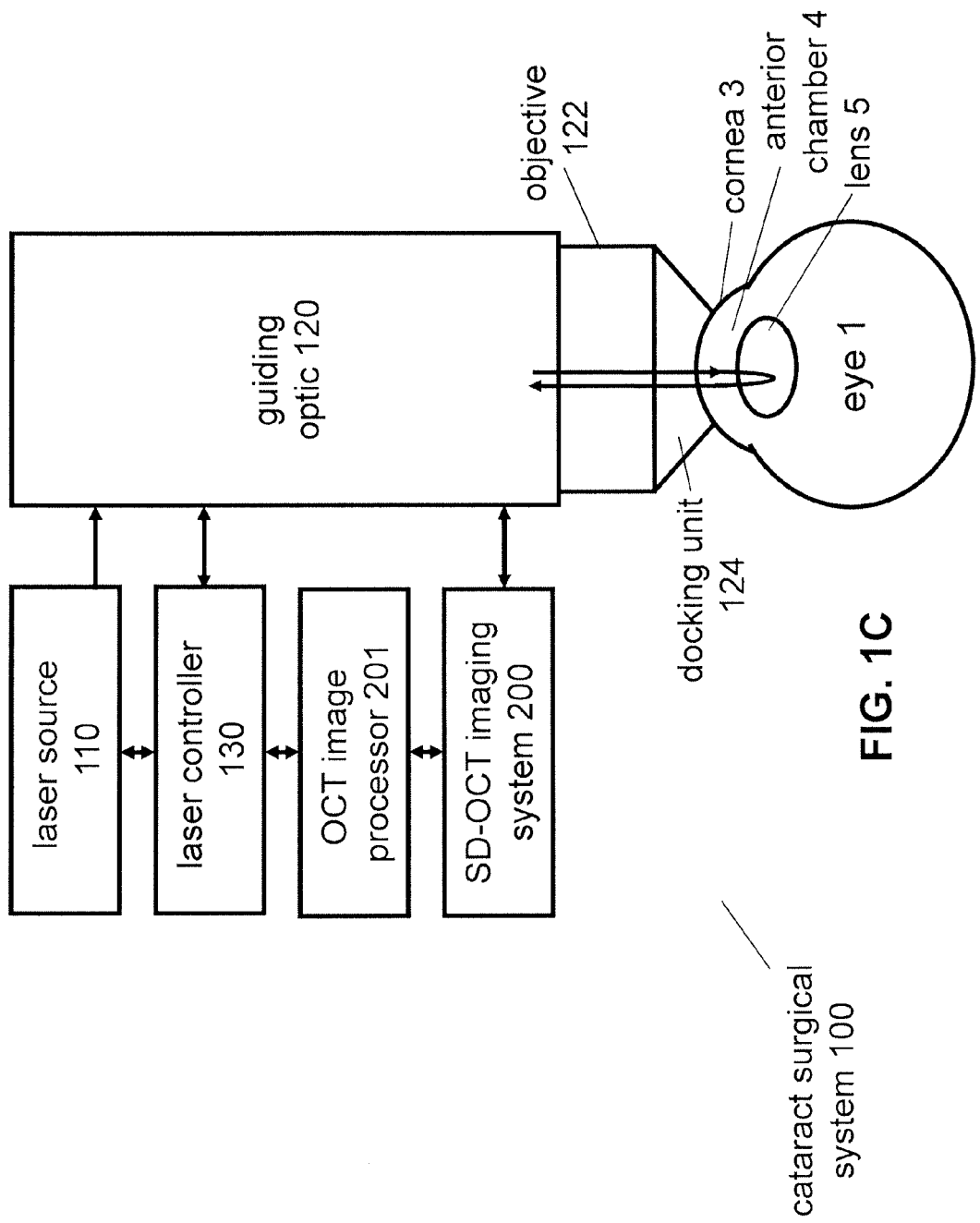
FIG. 1C illustrates an embodiment of a cataract laser surgical system.

In some embodiments, the SD-OCT imaging system 200 can be coupled to the laser controller 130, as in FIG. 1A, or the OCT image processor 201 can be a self-standing unit, directly coupled to SD-OCT imaging system 200 and to the laser controller 130, as in FIG. 1C. In these embodiments, the OCT image processor 201 can generate control signals in relation to the image of the first photo-disrupted region 306 and can apply the generated control signals to the laser controller 130 to cause the laser controller 130 to generate the electronic representation of the modified scan pattern. The OCT image processor 201 can be fully or partially integrated into the SD-OCT imaging system 200 as in FIG. 1A.

Figure 1D:
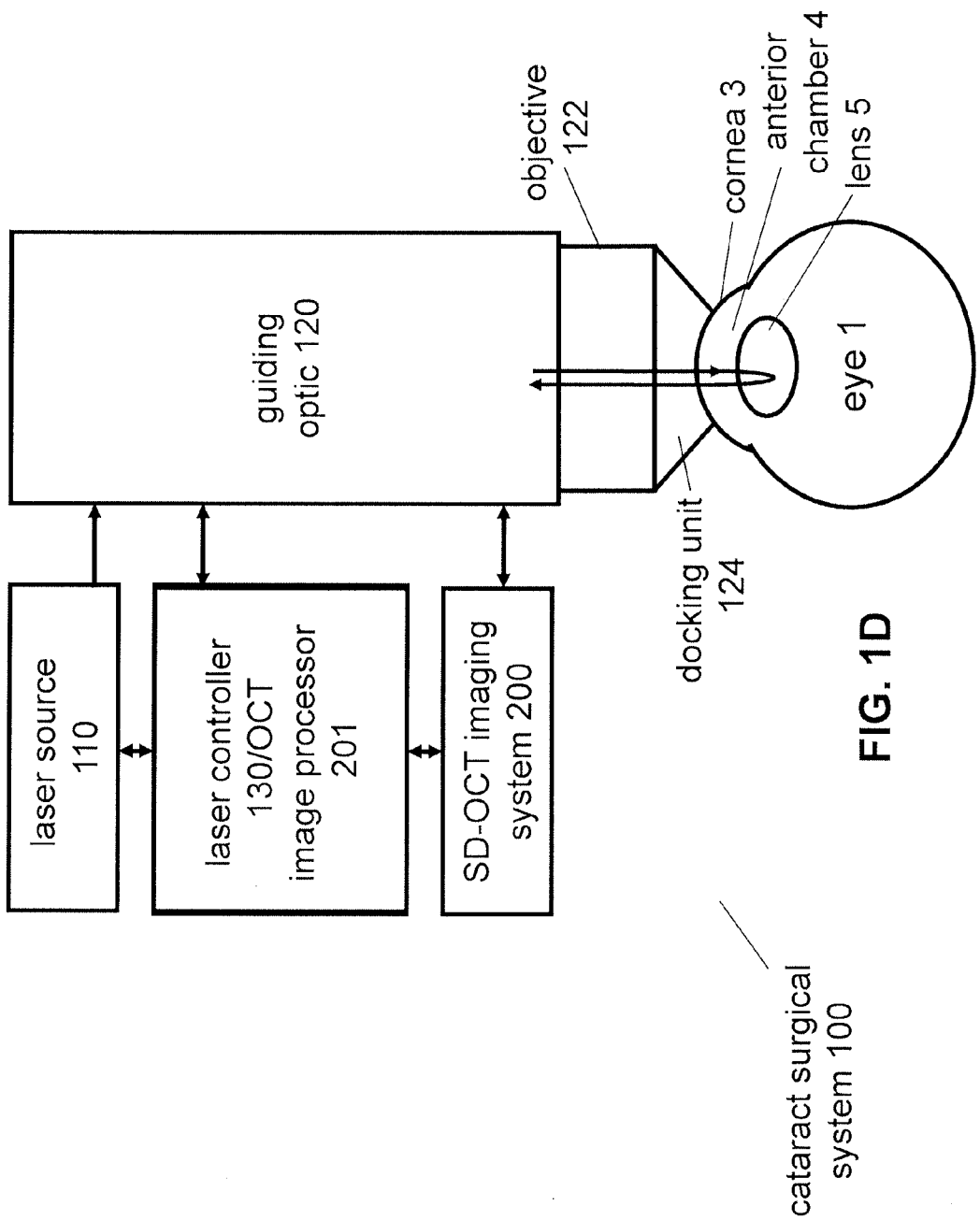
FIG. 1D illustrates an embodiment of a cataract laser surgical system.

FIG. 1D illustrates that in some embodiments the OCT image processor 201 can also be overlapping or even integrated with the laser controller 130. The embodiments of FIGS. 1A, 1C and 1D illustrate that the software-related functions of processing the OCT image and generating the modified scan pattern can be partially or fully executed by a multi-purpose processor that can be housed in either the SD-OCT imaging system 200, or the laser controller 130, or in a block integrating both, or can be a self-standing block, separate from both.

As mentioned above, the unusually large z-depth range of cataract surgeries that can be larger than 4 mm or in some embodiments larger than 6 mm may require the use of a substantially more complex SD-OCT imaging system 200 than what is employed in corneal or retinal systems. Accordingly, in some embodiments the SD-OCT imaging system 200 can be configured to have an imaging or z-depth range Lmax larger than 4 mm, such as in the range of 4-20 mm. In other embodiments, the imaging or z-depth range Lmax can be larger than 6 mm, such as in the range of 6-10 mm.

Lmax, the imaging or z-depth range of SD-OCT imaging system 200 can depend on the wavelength $\lambda$ of the imaging laser beam 308, the wavelength resolution $\delta\lambda$, the Nyquist frequency Nf, the focal length f and the pupil d of the SD-OCT-imaging system 200, as described below in detail. Accordingly, embodiments of the SD-OCT imaging system 200 can be designed with parameters $\lambda$, $\delta\lambda$, Nf, f and d such that the imaging or z-depth range is larger than 4 mm, or in some embodiments larger than 6 mm.

The difficulty of extending the imaging depth range of a system from 1-2 mm to 4 mm or more can be also appreciated from the fact that some existing systems that require larger than 2 mm imaging ranges achieve this not by involving more advanced optics as that would have been prohibitively hard. Instead, these systems employ a conventional imaging system with a less than 2 mm imaging range and boost the imaging range of this conventional system by taking several images at adjacent z-depths separated by about 2 mm and generate a single image with the larger range by integrating the adjacent-depth images using a complex image recognition and processing circuitry. Such systems can be electronically complex and the image integration slows down the speed of their performance considerably. To avoid the substantial slowing down of the imaging performance and the need for complex electronics, implementations of the SD-OCT imaging system 200 achieve the imaging depth range of more than 4 or 6 mm without integrating two or more images.

For clarity, it is noted that it is customary to distinguish between two types of imaging scans: A-scans and B-scans. An A-scan refers to an image of the target in a range of z-depths corresponding to a single transverse (x,y) coordinate, in the reference frame whose z axis is aligned with an optical axis of the guiding optic 120. An A-scan can be obtained by directing an imaging beam of an imaging system to a single (x,y) point of the target and collecting the imaging information corresponding to different z-depths.

Some imaging systems generate an A-scan by indeed scanning the z imaging depth-range and recording the image data for different z-depths sequentially. However, while SD-OCT imaging systems, as explained below, collect the image data for different z-depths simultaneously, i.e. without scanning in the z direction, yet their images are still often referred to as A-scans.

A 13-scan refers to a set of A-scans that correspond to a set or line of (x,y) points, collected as the imaging beam is scanned along a transverse line or in a transverse scanning pattern. A typical B-scan with regular (x,y) resolution can include 500-2,000 A-scans. A B-scan with high (x,y) resolution can include 1,000-3,000 A-scans. Particularly high (x,y) resolution B-scans can include 2,000-5,000 or 2,000-16,000 A-scans. Typically, the B-scan can include these A-scans integrated into a cross sectional, circular or cylindrical image of the target. As such, a B-scan can provide a substantially more detailed and thus substantially more actionable feedback imaging information for the surgeon than an individual A-scan. Accordingly, in the embodiments of the cataract surgical system 100 an image of the first photo-disrupted region and the second photo-disrupted region can refer to a B-scan that can include 500-2,000, 1,000-3,000, 2,000-5,000, or 2,000-16,000 A-scans.

OCT imaging systems can be categorized into two classes: Time Domain, or TD-OCT imaging systems, and Spectral Domain, or SD-OCT imaging systems. TD-OCT imaging systems use an imaging light beam with a bandwidth suitable to define short pulse lengths and gather the imaging information from different z-depths sequentially, in essence scanning along the z axis. In contrast, SD-OCT imaging systems use an imaging light beam with a bandwidth where the different wavelength spectral components capture and carry imaging information representing different z-depth in parallel, at the same time. This allows the SD-OCT imaging systems to gather the imaging information from different z-depths simultaneously, in parallel. Parallel sensing of the z-depth imaging information accelerates the performance of the SD-OCT imaging systems by a factor of 10-1,000 relative to the TD-OCT imaging systems. This faster performance of the SD-OCT imaging systems can be utilized in several embodiments, as described next.

In terms of imaging times, this accelerated performance translates to embodiments of the SD-OCT imaging system 200 being able to generate a B-scan image after the photo-disruption started in an imaging time less than a surgical time. The imaging time can be less than 1 second, such as in the range of 0.1 msec-1 sec. In some embodiments the imaging time can be less than 0.1 second, such as in the range of 1 msec-0.1 sec. These short imaging times mean that the SD-OCT imaging system 200 can generate images that can provide timely and thus useful feedback about the progress of the cataract procedure for the surgeon so that the surgeon can modify the surgical procedure in response to the feedback. This modification can include entering a modified target scan pattern.

The next level of utility is offered by some embodiments of the SD-OCT imaging system 200 that can provide feedback images not only once but repeatedly during the cataract surgery. Such systems can provide valuable timely feedback regarding the development, location and growth of the first photo-disrupted region 306, thus offering qualitative improvement in the precision, performance and safety of the cataract surgical system 100.

Some embodiments of the SD-OCT imaging system 200 can offer further qualitative improvements. They can provide not only a few updated images during the cataract surgery, but an essentially live image of the progress of the procedure. An essentially live feedback can deliver highly valuable, timely, and actionable information for the surgeon to monitor the progress of the surgery, improve the surgical precision, detect undesirable outcomes early and react to them in real time.

An often used refresh rate of live video images is about 24 frames/second. Therefore, imaging systems that can provide images at a refresh rate or frame rate of 20 to 25 frames/second or higher can provide images that will appear essentially live for the surgeon. Whereas systems with a frame rate or refresh rate considerably less than 20-25 frames/second may not be perceived as live video imaging, but rather as jerky, jumpy images, possibly even distracting the surgeon from the cataract procedure.

In this context, because TD-OCT imaging systems acquire z-depth imaging information sequentially, they may be able to generate only low resolution B-scans with a refresh rate of only one or few frames per second. TD-OCT imaging systems that are expected to provide images with higher resolution may be forced to scan and refresh the images at an even lower rate, well below one frame/second. Such distinctly slower-than-live feedback images appear jerky for the surgeon and can even be a distraction. Moreover, the slow scanning speed and resulting slow refresh rate can make some TD-OCT imaging systems to display artifacts, such as steps or discontinuous jumps in the image of a layer that in reality is smooth.

In contrast, SD-OCT systems gather image data at an (x,y) point from all z-depths simultaneously, in parallel. These images are sometimes still called A-scans, even though no sequential z-scanning is involved. Because of the parallel or simultaneous nature of gathering the image-data from different depths, embodiments of the SD-OCT system 200 can acquire the A-scans 10-1,000 times faster than TD-OCT imaging systems, as discussed above. In particular, quality SD-OCT imaging systems 200 can acquire 10,000-100,000 A-scans per second, or equivalently, can have an A-scan acquisition rate of 10-100 kHz. High quality SQ-OCT imaging systems 200 can have an A-scan acquisition rate of 30-300 kHz, and particularly high quality SD-OCT imaging systems 200 can have an A-scan acquisition rate of 100 kHz-1,000 kHz, much exceeding the A-scan acquisition rate that can be achieved by TD-OCT imaging systems.

Clearly, the A-scan acquisition rate, or number of A-scans/sec, is approximately equal to the number of A-scans/B-scan times the number of images/sec, the image refresh rate. For example, at the quality A-scan acquisition rate of 10,000-100,000 A-scan/sec, or 10-100 kHz, images with the regular (x,y) resolution of 500-2,000 A-scan/B-scan can be captured at image refresh rates in the range of 5-200 frames/sec that includes the refresh rate range of 20-200 frames/sec. In another example, at the high quality A-scan acquisition rate of 30-300 kHz, images with the high (x,y) resolution of 1,000-3,000 A-scan/B-scan can be captured at image refresh rates in the range of 10-300 frames/sec that includes the 25-300 frames/sec range. Finally, at the particularly high quality A-scan acquisition range of 100-1,000 kHz, images with the particularly high (x,y) resolution of 2,000-5,000 A-scans/B-scan can be generated with image refresh rates in the range of 25-500 frames/sec.

These examples show that embodiments of the SD-OCT imaging systems 200 with various pairings of the A-scan acquisition rate quality and the A-scan/B-scan resolutions ratios can provide image refresh rates that are distinctly above the 20 frames/sec threshold live video rate and thus offer qualitative advantages over the TD-OCT imaging systems.

It is noted that embodiments of the SD-OCT imaging system 200 can be operated at image refresh rates lower than the live video rate, typically when operated with a particularly high resolution and a regular A-scan acquisition rate quality. Such embodiments may be used when the operator of the SD-OCT imaging system 200 calls for the particularly high resolution setting for medical reasons, willingly foregoing the live-video-rate capability of the SD-OCT imaging system 200.

The overall amount of image data can be captured in other ways as well. The specific design parameters of the SD-OCT imaging system 200, such as the full length of its sensor array control the z-directional distance of the resolved points, the z-resolution. This z-resolution can be, for example, a 5 micron z-directional distance between data points, translating to 1,000 z-depth points in a typical Lmax=5 mm z-depth range. In a regular (x,y) resolution embodiment, where a B-scan contains 500-2,000 A-scans, often spaced apart also by about 5 microns in the (x,y) plane, this embodiment can generate an image with an image-resolution of 0.5-2 million pixels per image. Other embodiments may be able to capture images with an image resolution of 1-3 million, 2-5 million, or even 2-10 million image points/frame, still providing the images at a live video rate of 20-200, 25-300, or 25-500 frames/sec or faster.

Because of these remarkably high (x,y), z- and image resolutions, embodiments of the SD-OCT imaging systems 200 can capture and display complex, sharp and detail-rich images. For example, the B-scans can include scanning the lens 5 along several circles, radial rays, spirals, and two dimensional (2D) transverse or lateral scanning grids in the (x,y) plane. These detailed images allow the SD-OCT imaging system 200 to map out the actual shape of the lens 5 instead of using models and relying on assumptions about its geometry and shape.

It is noted here that displaying the OCT images also takes time. Thus, the refresh rate of the image display, limited by the speed of the electronic performance of a display unit of the SD-OCT imaging system 200, might be lower than the rate of the OCT image acquisition-unit. In this context, the above cited refresh rates characterize the speed of image-acquisition by the SD-OCT imaging system 200, not the display rate of the display unit that can be slower, depending on the electronic and data-transfer limiting factors.

Given that the imaging speeds of the SD-OCT and TD-OCT imaging systems are on opposite sides of the live video-rate of 20-25 frames/second, embodiments of the cataract surgical system that include the SD-OCT imaging system 200 can be capable of providing timely and smooth live feedback information for the surgeon that are free of motional artifacts, whereas those that use typical TD-OCT imaging systems are not capable of providing such smooth live feedback for the surgeon and are prone to display motional artifacts.

A final factor, impacting the long term performance of embodiments of the SD-OCT imaging system 200 is that SD-OCT imaging systems do not have moving parts and thus their reliability and serviceability is quite satisfactory. In contrast, TD-OCT systems have rapidly moving parts, associated with the movement of a reference mirror in a reference arm of the TD-OCT apparatus. Obviously, the presence of moving parts in the TD-OCT systems increases the chance of malfunction and misalignment, thus possibly decreasing their overall performance, demanding more frequent field-service and still facing the higher likelihood of long-term performance degradation.

In sum, SD-OCT imaging systems are qualitatively different from TD-OCT systems, especially for cataract applications, at least for the following reasons. (1) SD-OCT imaging systems are configured to provide live imaging or feedback images at refresh rates of 20-200, 20-300, or 20-500 frames/sec, useful for high precision cataract surgical processes, whereas TD-OCT systems are not. (2) SD-OCT imaging systems can provide images at live video rates with high (x,y) resolution of 500-2,000, 1,000-3,000, or 2,000-5,000 A-scan/B-scans or higher, whereas TD-OCT imaging systems cannot. (3) SD-OCT imaging systems can be operated with a quality A-scan acquisition rate of 10-100 kHz, 30-300 kHz, or 100-1,000 kHz, whereas TD-OCT system may not. (4) SD-OCT imaging systems are well suited to provide detail-rich images with high image resolution at live video rates, such as with 0.5-2, 1-3 or 2-5 million image points, whereas TD-OCT system are not. (5) SD-OCT imaging systems can provide images so rich in detail that an overall image of the lens 5 can be formed without using a model of the lens 5, whereas TD-OCT system cannot. (6) SD-OCT imaging systems typically do not display motional artifacts, whereas TD-OCT systems are likely to do so. (7) Finally, SD-OCT imaging systems require only infrequent field service and maintenance, such as only every 6 or 9 months, whereas TD-OCT imaging systems with their moving parts typically require field services and maintenance much more often.

An advantage of the SD-OCT imaging system 200 providing one or more feedback images or a feedback video of the cataract target region in general and the first photo-disrupted region 306 in particular is that the surgeon can react to the feedback and modify the surgery by generating a modified scan pattern in response to the provided feedback images or video. The modified scan pattern can be generated in different manners after the laser controller 130 generated the electronic representation of the original target scan pattern 302 according to an initial input received from a system operator.

In some embodiments, the laser controller 130 can generate the electronic representation of the modified target scan pattern according to a modification input also received from the system operator. In such embodiments, the modification input can be generated by the system operator in response to analyzing the image of the portion of the first photo-disrupted region 306. For example, the surgeon can study the image of the first photo-disrupted region 306, discover the formation of an undesirable gas bubble that would scatter the surgical laser beam excessively, and cause the generation of a modified scan pattern that steers the surgical laser beam 304 clear from the gas bubble.

In other embodiments, the SD-OCT imaging system 200 can display calibration marks to assist the surgeon or system operator to calibrate a location of the first photo-disrupted region 306 relative to the target scan pattern 302. Such calibration marks can be associated with characteristic points of the image, such as the apex of the cornea 3 or the lens 5.

In yet other embodiments, the SD-OCT imaging system 200 can include the OCT image processor 201. The OCT image processor 201 can analyze the image of the first photo-disrupted region 306 and display a feedback for the system operator. For example, if the OCT image processor 201 senses a miscalibration, i.e. that the first photo-disrupted region 306 is formed at a distance from where the target scan pattern 302 would have required, it can send a miscalibration feedback signal to the surgeon, who can then decide to stop the procedure and recalibrate the system, or to enter a modified scan pattern that compensates the miscalibration distance.

In yet other embodiments, the SD-OCT imaging system 200 can take a reference image before the first set of surgical laser pulses were generated and a feedback image after the first set of laser pulses generated the first photo-disrupted region 306. The OCT image processor 201 can determine the differences between the two images and display indications of these differences. The determined and displayed differences can allow the surgeon or the OCT image processor 201 to monitor the progress of the cataract surgery, to track discrepancies relative to the target scan pattern 302, including the appearance of unintended surgical byproducts, such as gas bubbles in a timely manner, and to cause the generation of the modified scan pattern in response to the image and displayed differences.

Finally, in some embodiments the OCT image processor 201 can play a more advanced and active role. For example, the OCT image processor 201 can actively analyze the image of the first photo-disrupted region 306 and generate a control signal to cause the laser controller 130 to generate the electronic representation of the modified scan pattern without necessarily waiting for a modification input from the surgeon. For example, if the OCT image processor 201 discovers an imminent high risk situation, such as the first photo-disrupted region getting formed too close to the posterior capsular layer, then it can stop the cataract procedure without waiting for the outcome of a slow and time-consuming interaction with the surgeon.

The above five embodiments can be combined in various ways. For example, upon determining from the image that a high risk situation is imminent, the OCT image processor 201 can both display a feedback signal for the surgeon and prepare a control signal for the laser controller 130 to stop the procedure. The OCT image processor 201 can then wait for a modification input from the surgeon for a predetermined time. In the absence of such a modification input within the predetermined time, the OCT image processor 201 can proceed with an action on its own to prevent the impending high risk situation and send the control signal to the laser controller 130 to stop the procedure without further waiting for an input from the surgeon.

FIGS. 2A-B illustrate the particular example of the laser controller 130 having planned the target scan pattern 302 in the posterior region of the lens 5. The cataract surgical system 100 may apply the surgical laser beam 304 according to the target scan pattern 302, creating the first photo-disrupted region 306. However, the subsequent imaging of the first photo-disrupted region 306 with the imaging laser beam 308 may reveal that the first photo-disrupted region 306 may have been formed misplaced by a deviation 310 from its intended target scan pattern 302. The deviation 310 can be a deviation of a location, an orientation or a shape of the first photo-disrupted region 306 relative to the target scan pattern 302. This misplacement or miscalibration can happen for a variety of reasons: a mistaken input by the surgeon, a manufacturing imprecision of the production process of the guiding optic 120, a thermal expansion of the components, a movement by the patient after the initial imaging, a deformation of the eye caused by the pressure of the patient interface 124, or a mischaracterization of the refractive properties of the eye 1 during a preoperative diagnostic process, among others.

FIG. 2B illustrates that in some embodiments, the SD-OCT imaging system 200 can display the feedback image of the target scan pattern 302 and the image of the first photo-disrupted region 306 without an analysis. From this feedback image the surgeon can visually determine the deviation 310 and enter a compensating modification input to cause the laser controller 130 to modified scan pattern 312. In other embodiments, the SD-OCT imaging system 200 can display calibration marks to assist the surgeon's analysis.

In other embodiments, the OCT image processor 201 can determine the deviation 310. Then, in some embodiments the OCT image processor 201 can display the determined deviation 310 as well as the feedback and recommendation for the surgeon, such as a suggested magnitude and direction of a shift of the scan pattern, or a warning sign for the surgeon. In these embodiments, the surgeon can enter a modification input into the laser controller 130 to cause the generation of a modified scan pattern 312 with the goal of reducing the deviation 310 to the reduced deviation 310r. In yet other embodiments, the OCT image processor 201 can directly signal the laser controller 130 to generate the electronic representation of the modified scan pattern 312 to reduce the determined deviation 310 to the reduced deviation 310r, all without waiting for a modification input from the surgeon.

FIG. 2B illustrates that the generation of the modified scan pattern 312 can take into account the miscalibration of the guiding optic 120 in any of the above embodiments. The modified scan pattern 312 can be shifted from the target scan pattern 302 by about the miscalibration of the guiding optic 120 so that when the surgical laser beam 304 forms a second photo-disrupted region 314 misplaced from the modified scan pattern 312 because of the miscalibration of the guiding optic 120, the second photo-disrupted region 314 ends up close to the originally intended target scan pattern 302, reducing the deviation 310 to the reduced deviation 310r.

Figure 2C:
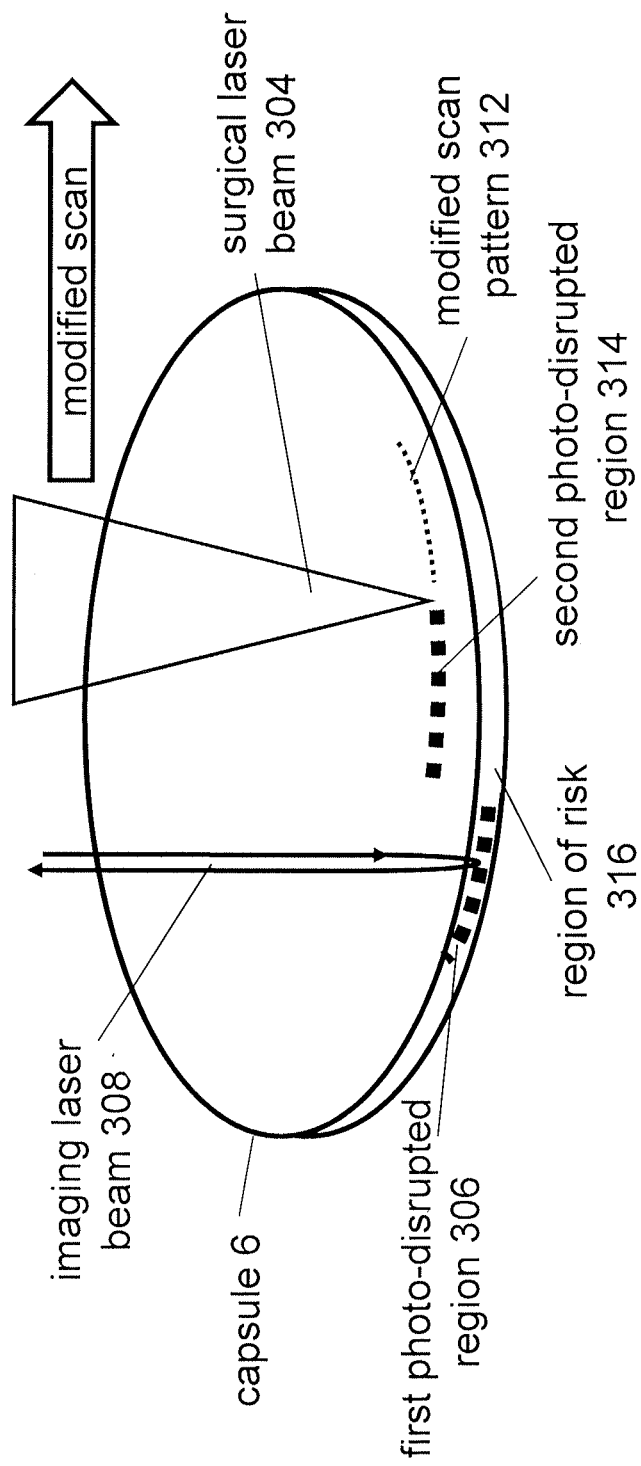

FIG. 2C illustrates a related embodiment, where the OCT image processor 201 can determine whether the first photo-disrupted region 306 got formed or extended inadvertently into a region of risk 316. The first photo-disrupted region 306 being formed in the region of risk 316 endangers the integrity of the posterior capsule layer and can breach it, puncturing the capsule 6 and necessitating a complex vitrectomy procedure. This would substantially elevate the risk of the cataract procedure.

To preempt such a breach, in various embodiments the OCT image processor 201 can analyze the feedback image or images, or the essentially live imaging of the SD-OCT imaging system 200 to monitor whether the first photo-disrupted region 306 was formed too close to or in the posterior capsule layer, in the region of risk 316. If the OCT image processor 201 senses that the first photo-disrupted region 306 has been formed in this region of risk 316, then the OCT image processor 201 can either display a warning feedback for the surgeon, or can generate a control signal for the laser controller 130 to cause the generation of the modified scan pattern 312. In all the above embodiments, the laser controller 130 can generate the modified scan pattern 312 and direct the surgical laser beam 304 accordingly to form the second photo-disrupted region 314 outside the region of risk 316.

In some embodiments, the OCT image processor 201 and the laser controller 130 can be partially or fully integrated. For example, a single integrated processor can perform both the image processing function of the OCT image processor 201 and the scan pattern generating function of the laser controller 130.

FIGS. 3A-E illustrate an embodiment where the target scan pattern 302 is a chop pattern. In some cases the cataract surgeon may choose to chop the lens into 2, 4 or 6 portions to facilitate their removal or aspiration through the capsulotomy.

FIGS. 3A-B illustrate that in the design phase of the cataract surgery, upon receiving the corresponding input from the surgeon, the laser controller 130 may generate a target scan pattern 302 that consists of points on two chop planes, formed in the (x,z) and (y,z) planes, for example. In an ideal cataract procedure, when the first set of laser pulses are applied to this target scan pattern 302, the generated first photo-disrupted region 306 includes four chop planes, chopping the lens into four segments along these chop planes.

FIG. 3C-D illustrate that, in non-ideal cases, after the first set of laser pulses of the surgical laser beam 304 have been directed to the points of the target scan pattern 302 and the first photo-disrupted region 306 started to form, an unintended surgical byproduct 320 can form as well. This surgical byproduct 320 can be a group of the freshly formed photo-disruption bubbles coalescing into a single large bubble that can scatter or redirect the subsequent laser pulses in unintended directions, such as towards the retina, possibly causing damage and phototoxicity. Therefore, the precision of the photo-disruption process can diminish and its risk can increase if subsequent laser pulses are directed into the gas bubble 320.

Such as unintended development can be preempted by an OCT image processor 201 that can recognize the formation of the gas bubble or another surgical byproduct 320 from analyzing the images of the SD-OCT imaging system 200. And since the SD-OCT images can be generated at an essentially live rate, the OCT image processor 201 can relay this recognition as a timely and actionable feedback either for the surgeon or for the laser controller 130, prompting a modifying response, as described next.

FIGS. 3C-D illustrate that the feedback can take the form of the OCT image processor 201 analyzing the image, determining a recommended degree of rotation of the chop pattern and displaying the recommended rotated chop pattern for the surgeon to enter the corresponding modification input. In other embodiments, the OCT image processor 201 can apply a control signal to the laser controller 130 directly to generate an electronic representation of a rotated chop pattern as the modified scan pattern 312 such that the rotated chop pattern 312 is non-overlapping with the gas bubble 320. The rotated chop pattern 312 can extend through the entire z-depth range of the lens 5, in effect starting the procedure over, or can be a partial chop pattern, continuing the cutting from the z-depth where the original target scan pattern 302 was abandoned.

FIG. 3E illustrates that the OCT image processor 201 could recommend to direct the surgical laser beam 304 to the points of the modified or rotated scan pattern 312 to form the second or rotated or modified photo-disrupted region 314 that does not overlap with the coalesced bubble 320. This embodiment thus avoids the surgical laser beam 304 being scattered into unintended directions, reducing the risk of the cataract procedure.

FIG. 4A illustrates an alternative embodiment of forming a modified or non-overlapping scan pattern 312 in response to the OCT image processor 201 sensing the emergence of the surgical byproduct 320. Here, the modified or non-overlapping scan pattern 312 does not include rotated chop planes. Instead, the overlap is avoided by the surgical laser beam 304 being scanned according to the unchanged target scan pattern 302 but the laser controller 130 blanking out the laser pulses that would be directed into the surgical byproduct bubble 320. The laser controller 130 can un-blank the laser pulses to hit all the points of the target scan pattern 302 once the scanning moved past the surgical byproduct bubble 320.

FIG. 4B illustrates yet another embodiment where once the OCT image processor 201 recognizes that continuing the scanning of the surgical laser beam 304 along the original target scan pattern 302 would create a first photo-disrupted region 306 overlapping with the surgical byproduct bubble 320 by analyzing the feedback images or the live rate image stream of the SD-OCT imaging system 200, it can simply stop the scanning of the surgical laser beam 304. In some embodiments, after the stopping the OCT image processor 201 or the laser controller 130 can display a prompt for the system operator, asking for a modification input or corrective action.

In some surgical scenarios, multiple bubbles 320-$i$ may form more or less simultaneously. Therefore, some embodiments of the cataract surgical system 100 can be configured to generate a modified scan pattern 312 that avoids multiple bubbles simultaneously.

FIGS. 4C-D illustrate that in some embodiments the OCT image processor 201 can be configured to analyze a portion of the image that is distinct from the first photo-disrupted region 306, and to generate a feedback based on this analysis. In this particular example, the formation of the first photo-disrupted region 306 can cause the lens 5 and thus the lens capsule 6 to expand, as indicated by the arrow. The SD-OCT imaging system 200 may image this expanded anterior capsular layer 322. The OCT image processor 201 may analyze this image and determine the shift of the location of the expanded anterior capsular layer 322.

Knowing the location of the anterior capsular layer is important for a cataract procedure because in some embodiments the capsulotomy target scan pattern 324 is placed to cut through the anterior capsular layer. If the capsulotomy target scan pattern 324 is placed according to an image taken before the capsular expansion, then the surgical laser beam 304 will attempt to create the capsulotomy at an incorrect location.

FIG. 4D illustrates that to prevent this from happening, the OCT image processor 201 can determine the shift of the location of the expanded anterior capsular layer 322 and either display this shift for the system operator to enter a modification input into the laser controller 130, or signal this shift directly to the laser controller 130, in either case to cause the laser controller to generate a modified capsulotomy scan pattern 326 that properly generates the capsulotomy in the expanded capsule.

FIGS. 5A-D illustrate another embodiment in connection to forming a laser-assisted capsulotomy or incision. In this embodiment, the OCT image processor 201 can analyze the repeated feedback images or live streaming images and identify an uncut portion or "tag" 330 within the first photo-disrupted region 306 where the efficiency of the photo-disruption was limited and thus the anterior capsular membrane was not cut fully through, leaving the uncut portion or "tag" 330 behind. Such tags 330 can elevate the risk of tearing the capsule or capsular membrane when the capsular lid or cap is removed by the surgeon. To prevent such an undesirable or high risk outcome, the OCT image processor 201 can either display a recommendation for the surgeon how to remove the tag 330 by scanning along an additional modified scan pattern 312, or can apply a control signal to the laser controller 130 directly to generate the electronic representation of the modified scan pattern 312 to rescan at least the tag 330 to generate a re-scanned tag-region 332 as the second photo-disrupted region 314. With this re-scanning, the first photo-disrupted region 306 and the second photo-disrupted region 314 can form a completed photo-disrupted region 334, in this case a completed capsulotomy 334, allowing the surgeon to remove the capsular lid or cap with a minimal risk of tearing.

Figure 6:
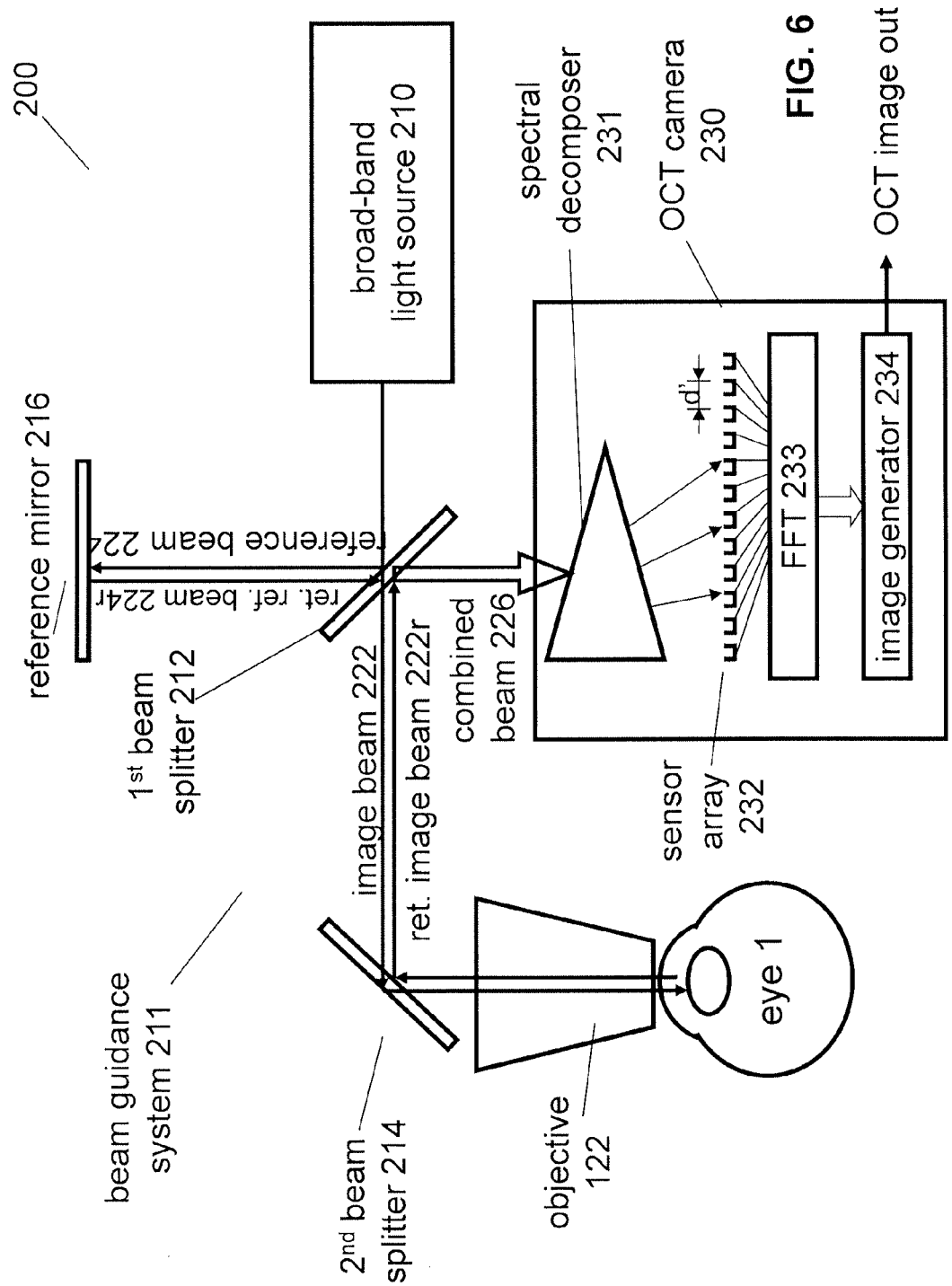
FIG. 6 illustrates an embodiment of a Spectral Domain Optical Coherence Tomographic imaging system.

FIG. 6 illustrates that in some embodiments the SD-OCT imaging system 200 can comprise a Spectrometer-Based-OCT (SB-OCT) imaging system 200 that includes a broad-band light source 210 to generate a broad-band light or laser beam. The broad-band beam can have a mean wavelength $\lambda_0$ and a relatively broad bandwidth $W_{source}$. In some typical examples, $\lambda_0$ can be in the 800-1100 nm range, and $W_{source}$ can be in the 10-150 nm range.

The broad-band beam can be coupled into a beam guidance system 211 that can include a $1^{st}$ beam splitter 212. The $1^{st}$ beam splitter 212 can split the broad-band beam into an image beam 222 and a reference beam 224. The image beam 222 can be guided by a $2^{nd}$ beam splitter 214 into the main optical pathway of the guiding optic 120, and from there on through the objective 122 and possibly the patient interface 124 to the eye 1. The beam guidance system 211 can also guide a returned image beam 222$r$ from the eye 1 to the $1^{st}$ beam splitter 212. The image beam 222 and returned image beam 222$r$ were previously referred to jointly as the imaging laser beam 308.

In addition, the beam guidance system 211 can guide the reference beam 224 to a reference mirror 216, guide a returned reference beam 224$r$ from the reference mirror 216, and combine the returned image beam 222$r$ and the returned reference beam 224$r$ into a combined beam 226 at the $1^{st}$ beam splitter 212. The combined beam 226 carries the imaging information from the eye 1 in the interference of the returned image beam 222$r$ and the returned reference beam 224$r$. Some embodiments may use other types of delay elements in place of or in conjunction with the reference mirror

216. Others may use yet another beam splitter for combining the returned image beam 222*r* and returned reference beam 224*r*. In some embodiments, the beam guidance system 211 can include a Mach-Zehnder interferometer. Such systems may have favorable noise reduction properties.

TD-OCT imaging systems capture the imaging data from the different z-depths in the z imaging range sequentially by moving the reference mirror 216 in a corresponding distance range for each (x,y) point separately, essentially like a Michelson-Morley interferometer. In contrast, SD-OCT imaging systems use the different spectral components of the broad-band imaging light to capture the imaging data from different z-depths in parallel. The SD-OCT imaging systems can be thought of as many Michelson-Morley (MM) interferometers operating at different wavelengths in parallel. Since the MM systems operating at different wavelengths image the eye 1 at different z-depths, the combined beam 226 of an SD-OCT system 200 carries the imaging data or information from all z-depths of the eye 1 simultaneously and thus does not require the movement or scanning of any mechanical system component, such as the reference mirror 216. As discussed above, this absence of mechanical scanning for SD-OCT systems translates to an acceleration of the imaging speed by a factor of at least 10, or more typically 100-1,000 relative to TD-OCT imaging systems.

The SD-OCT imaging system 200 can also include an OCT camera 230, configured to receive the combined beam 226. To recover the image information for all z-depths, the combined beam 226 can be decomposed into its spectral components by a spectral decomposer 231 such as a prism or grating. Each spectral component with δλ bandwidth around a wavelength 2 and the interference information they carry can be sensed in parallel by individual sensors of a sensor array 232, the sensors being separated by a distance d' from each other. The interference information sensed by the sensors individually can then be used to reconstruct the image of the entire z-depth range by a Fast-Fourier-Transformer (ITT) system 233 to generate a Fourier transform from the sensed spectral components. In effect, the interference data or information carried by the different wavelength components can be translated into a simultaneous or essentially instantaneous "z-scanning" of the imaged z-depth range. This translation of the interference data into "z-scan" data can be carried out by an image generator 234 to generate and output an OCT image from the Fourier transform of the sensed spectral components.

Some embodiments of the OCT camera 230 may use CCD (charge-coupled device) pixels as the sensors of the sensor array 232. Other embodiments can achieve improved readout speeds by using CMOS sensors. In such embodiments, the CMOS sensors can be read out in parallel. Further, in CMOS embodiments, it is possible to read out only sensors or pixels of interest, either selected prior to the imaging, or selected in real time based on whether their content changed because of the imaging. Both of these aspects make CMOS pixels quite useful for speeding up the performance of the OCT camera 230.

Using standard optical analysis, the critical imaging and performance parameters of the SD-OCT system 200 can be characterized by its architectural and design parameters as follows. Since the spectral decomposer 231 directs the different wavelength components of the combined beam 226 into slightly differing directions, the smaller and more densely packed the individual sensors or pixels are (the smaller d' is), the narrower δλ wavelength/spectral ranges are resolved by the OCT camera 230. The other quantity, determining δλ besides the pixel density, is the total range of wavelengths, i.e. the bandwidth $W_{camera}$ of the OCT camera 230. In a simple arrangement, δλ is proportional to the bandwidth $W_{camera}$ and inversely proportional to the number of pixels in a row of the sensor array 232.

The important imaging z-depth range, or z-imaging range, Lmax is intimately related to δλ: the narrower the δλ wavelength ranges, the broader the imaging range in the z direction because these two quantities are connected by an inverting Fourier transform. In particular, the theoretical maximum imaging range is given by $$L\max = \frac{1}{4}\left(\frac{\lambda_0^2}{\delta\lambda}\right) = \frac{1}{2}\frac{1}{Nf} \qquad (1)$$

Here, the value $\lambda_0$ refers to the average or central wavelength of the broad-band light source 210 and Nf denotes the Nyquist frequency of the OCT camera 230. In reality, additional factors may limit the effective imaging range below this theoretical maximum, such as the signal to noise ratio. Therefore, the effective imaging range is typically smaller than this theoretical value Lmax.

One factor that can limit the imaging range further is the Rayleigh range R. R can be expressed using Δx, the resolution in the transverse x direction, or "transverse resolution", governed by the numerical aperture NA and the wavelength $\lambda_0$ of the light source 210. Specifically, Δx can be expressed as:

$$\Delta x = \frac{4}{\pi}\left(\lambda_0 \frac{f}{d}\right) \qquad (2)$$

where f is the focal length and d is the pupil of the objective 122, their ratio determining NA. Using Δx, the above discussed Rayleigh range R can be expressed as:

$$R = \frac{\pi}{2}\left(\frac{(\Delta x)^2}{\lambda_0}\right) \qquad (3)$$

The Rayleigh range R is often defined as the z directional distance between the focal depth and the depth where the beam's width is $\sqrt{2}$ times the width at the focal depth. Thus, R characterizes the z-range within which the beam is narrow enough to enable high resolution imaging as limited by geometrical and wave optics. In this context, Lmax can be thought of as characterizing the z-imaging range as limited by the light source 210 and the resolution of the sensor array 232. A system design principle often thought of as optimal, e.g. for Gaussian beams, is to make these two z-ranges align with each other. For example, in some implementations, Lmax can be chosen to be essentially equal to 1-6 R:

$$L\max=1,\ldots 6R \qquad (4)$$

The same design principle can be stated through the concept of the widely used "depth of focus", which is often defined as twice the Rayleigh range.

As shown by Eqs. (1)-(4), the z-imaging range depends on Lmax and R, which in turn depend on the system design parameters including $\lambda_0$, δλ, $W_{camera}$, $W_{source}$, f, d',Nf and d. Thus, for imaging systems for cataract surgery, the above system design parameters are to be chosen such that the z-depth imaging range of the SD-OCT imaging system 200 exceed 4 mm or 6 mm, such as to fall in the range of 4-20 mm or 6-10 mm, thus making the cataract surgical system 100 capable of assisting cataract surgeries by high resolution and sufficiently fast imaging. This design requirement is quite demanding and distinguishes cataract imaging systems from corneal or retinal imaging systems.

Figure 7:
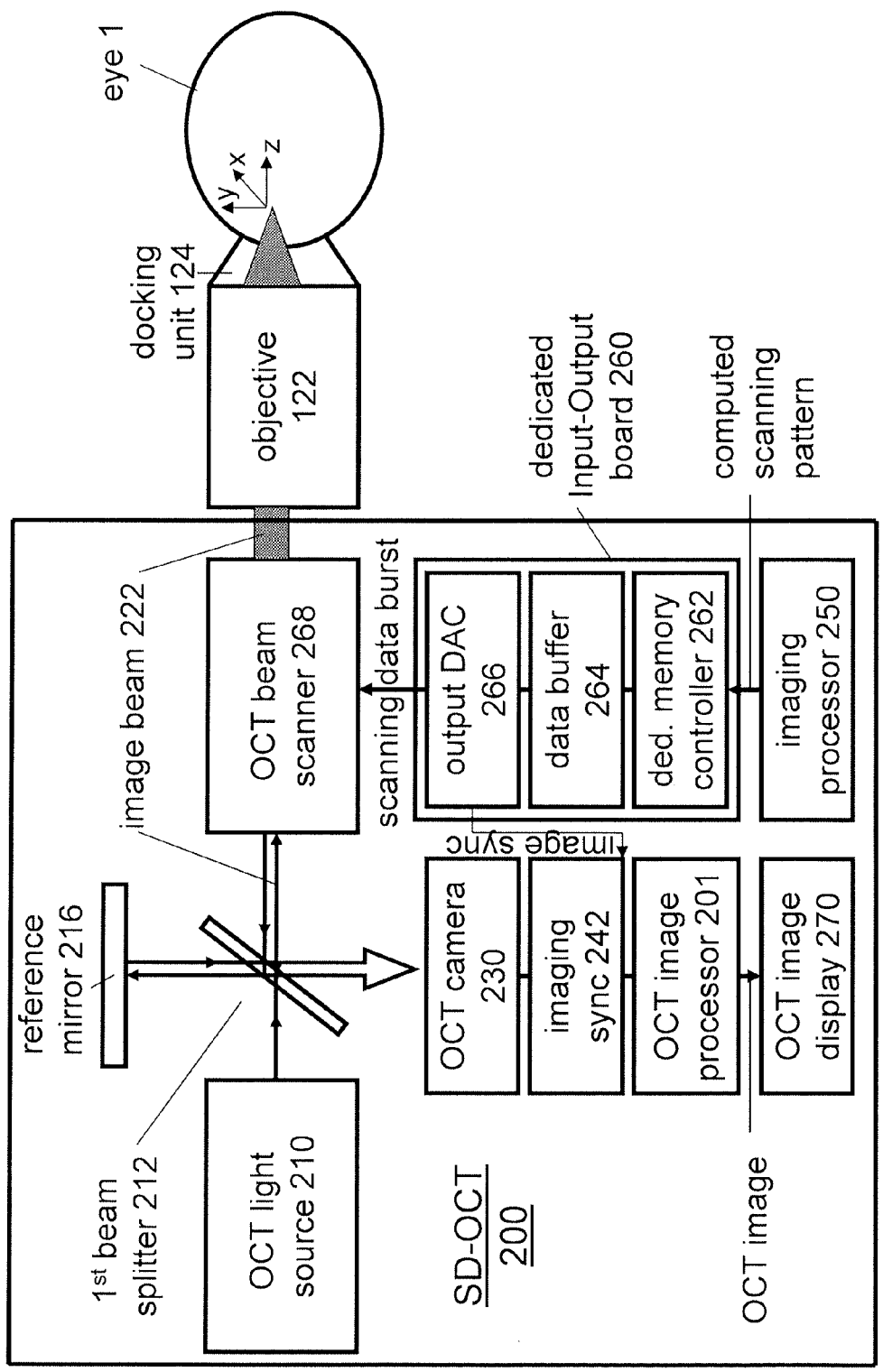
FIG. 7 illustrates an embodiment of a Spectral Domain Optical Coherence Tomographic imaging system with a dedicated Input-Output board.

FIG. 7 illustrates an embodiment that can ensure not only a large z-depth imaging range, but a fast imaging time, allowing the SD-OCT imaging system 200 to provide feedback images in a timely and thus actionable manner, including operating at an essentially live video rate. As discussed above, a cataract surgical system 100 with the SD-OCT imaging system 200 can have its control system, including the OCT image processor 201 and the laser controller 130 operate in essentially real time, with the option of adjusting or modifying the surgical scan patterns during the surgery according to the received feedback imaging information.

As described below in detail, embodiments of FIG. 7 are also configured to scan the OCT imaging beam 308/222 particularly fast, using precomputed scan patterns. In some embodiments, these fast imaging refresh rates of the SD-OCT imaging system 200 can be achieved by including a dedicated Input-Output board 260.

One function of the dedicated Input-Output board 260 is to address problems of some existing OCT imaging systems that do not have circuitry and a processor dedicated to imaging. In these systems, the processor that is in charge of imaging can be forced or prompted to multitask and perform more than one function in an interleaved, parallel or overlapping manner. To carry out these functions, the imaging processor may perform an "interrupt" by switching from e.g. the task of scanning the imaging beam 222/308 to another task and back. Such interrupts, however short, can cause problems, since during the time when the scanning is stopped or frozen by the interrupt, the laser beam may remain pointed to the same position. This scanning-freeze can disrupt the timing of the (x,y) scan, introducing an error and noise into the coordinates of the imaged locations. This timing error in the outputted scanning data can reach delays of 50, 100 or more microseconds: a phenomenon sometimes called jitter.

In addition, typically several other input/output agents communicate on the same system bus on which the imaging processor is driving the scanning of the imaging beam, all demanding a fraction of the bus's cycle time. This shared nature of the channel allows it to support only slow data transfer rates, unfortunately. Further, to manage these competing demands, a portion of the cycle of the system bus is typically taken up by control signals. Therefore, even if an OCT imaging system is designed to avoid the scanning-freeze by switching the imaging processor to outputting the scanning data to the scanning unit in a single-task mode through a dedicated link, then the imaging processor will not be able to perform its other functions during this outputting step, such as computing the next scanning pattern. All these constraints slow down the performance of such existing imaging systems considerably.

Implementations of the SD-OCT imaging system 200 can overcome these difficulties by employing the following efficient design. The scanning of the image beam 222 can be controlled by an imaging processor 250 and a dedicated Input-Output board 260. The imaging processor 250 can compute scanning data such as the target scan pattern 302 and the modified scan pattern 312. These scanning data can include e.g. a sequence of (x,y) coordinates where the OCT image beam 222 is to be directed in the cataract target region. The imaging processor 250 can compute the scanning data as well as perform its other functions in connection to a storage medium that stores a computer code or instruction set to facilitate these functions of the imaging processor 250.

The dedicated Input-Output board 260 can include a local or dedicated memory controller 262, also referred to as a direct memory access (DMA) engine 262. The DMA engine/memory controller 262 can manage a transfer of the computed scanning data, indirectly or directly, from the imaging processor 250 toward a data buffer 264. The data buffer 264, coupled to the local memory controller 262 can store the scanning data and can be operable to output the scanning data towards an output digital-analog converter (output DAC) 266 at a high speed. The output DAC 266 can be coupled to the data buffer 264 to receive the scanning data, to convert selected outputted scanning data to analog scanning signals, and to output the scanning signals towards an OCT beam scanner 268 e.g. in a scanning data burst mode.

The image beam 222 can be scanned by the OCT beam scanner 268 through a separate dedicated imaging optic, or partially through the guiding optic 120 of the surgical beam. In either of these implementations, the image beam 222 can be coupled into the eye through the objective 122 and the corresponding docking unit or patient interface (PI) 124. In other embodiments, the image beam 222 can be guided into the eye 1 through air without the docking unit 124 being docked to the eye 1.

The output of the scanning data by the output DAC 266 can be synchronized by an imaging sync 242 to the operation of the OCT camera 230, so that the OCT camera 230 can take the OCT images synchronously with the scanning operations. The synchronously taken OCT images can be outputted to the OCT image processor 201 that can perform any one of the large number of image processing tasks described up to now. Finally, the generated and processed images can be displayed by an OCT image display 270. In some embodiments, the imaging processor 250 and the OCT image processor 201 can be integrated partially or completely.

Figure 8:
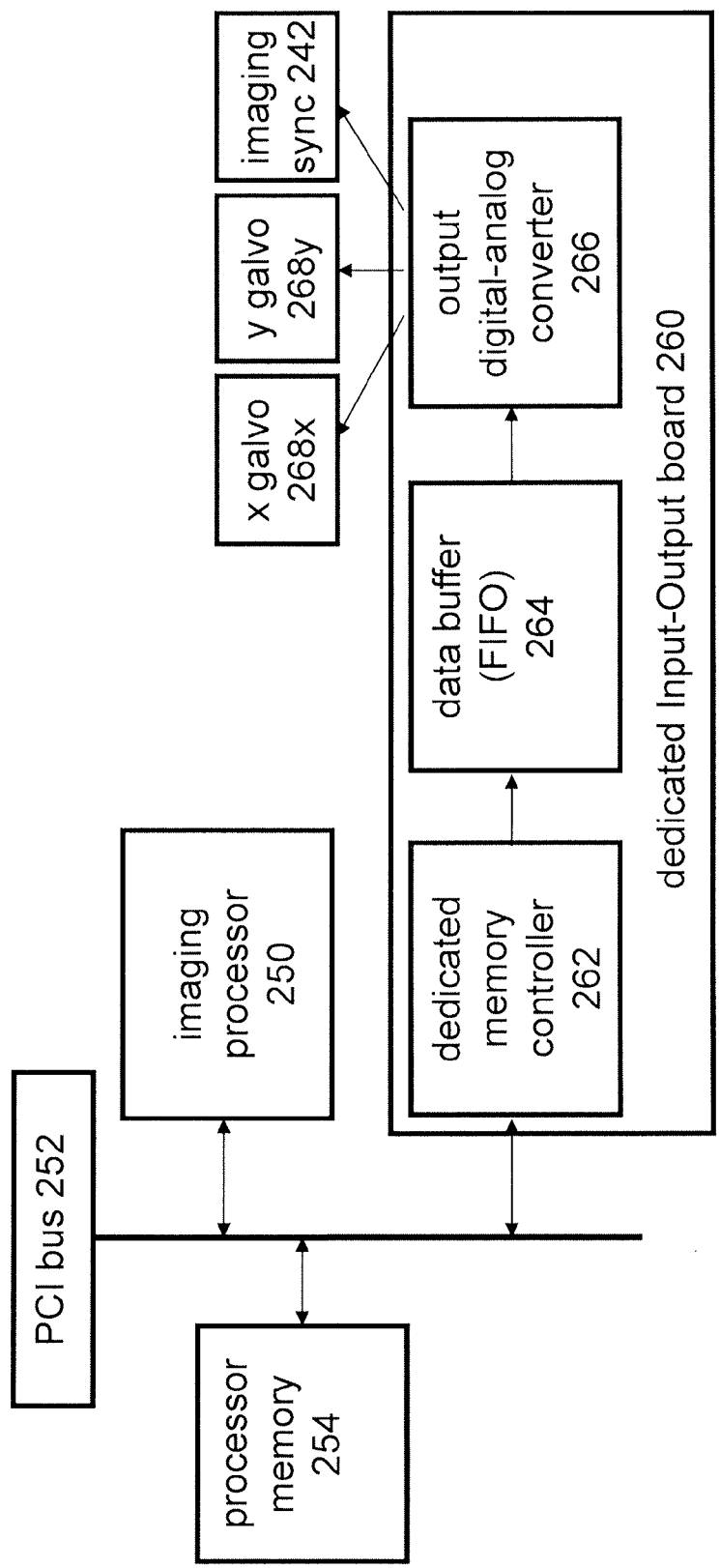
FIG. 8 illustrates a dedicated Input-Output board.

FIG. 8 illustrates an implementation of the dedicated Input-Output board 260 in some more detail. The imaging processor 250 can be coupled to a bus 252, such as a PCI bus 252. The system can also include a processor memory 254. The imaging processor 250 can compute the scan patterns and then output the computed scan patterns through the shared PCI bus 252 to the processor memory 254. After the imaging processor 250 generated the scan patterns but before the commencement of the actual scan operation, the dedicated DMA engine 262 can transfer the scanning data from the processor memory 254 to the data buffer 264. The data buffer 264 can be a first-in-first-out (FIFO) memory 264. The FIFO data buffer 264 can store the scan pattern or scanning data and output the stored scanning data to the output DAC 266 when prompted by the dedicated DMA engine 262. The output DAC 266 can convert the scanning data into analog scanning signals and output them to an x galvo beam scanner 268x and a y galvo beam scanner 268y of the OCT beam scanner 268 that control x and y galvo mirrors, or redirector elements, to scan the OCT image beam 222/308 according to the target scan pattern 302 and the modified scan pattern 312, coded in the scanning data. Some implementations may have an integrated (x,y) galvo-controller 268xy that controls a single galvo mirror capable of rotating around both the x and y axes. The output DAC 266 can also drive the image sync 242 to synchronize the taking of the OCT images with the scanning operations.

In some implementations, the imaging processor 250 can output the scanning data to the dedicated Input-Output board 260 through a dedicated memory bus or through a local bus instead of the shared PCI bus 252. In other implementations, there can be even a direct connection between the imaging processor 250 and the DMA engine 262.

This design is efficient at least for the following reasons. (1) The scanning data or scan patterns are pre-computed by the imaging processor 250, thus no time consuming real-time scanning data computation is involved. (2) The imaging processor 250 is not tasked with outputting the scanning data in real time, as the pre-computed scanning data are stored in the dedicated data buffer 264. This design can reduce interrupts, freezes and jitters below 50, 40, or even 20 microseconds, caused by the imaging processor 250 multitasking. (3) The transfer of the scanning data will not be interrupted by the bus 252 being shared by other agents, neither will it be slowed down by the typically slow transfer rates of the shared PCI bus 252. (4) The data buffer 264 is dedicated to the task of scanning, so the output of the scanning data can be performed in a fast transfer mode, such as a burst mode, further accelerating the scanning speed.

In addition, since the dedicated Input-Output board 260 drives the outputting of the scanning data essentially autonomously, the imaging processor 250 is free to perform other functions in parallel with the scanning data output, such as generating the modified scan pattern 312.

In some implementations, the speed of the output by the output DAC 266 can be so fast that an operating speed of the SD-OCT imaging system 200 can be limited by an integration time of the OCT camera 230 instead of the speed of the scanning electronics. In some of these implementations, the output DAC 266 can output the scanning signals at a rate within one of the following ranges: 1 Hz-1 MHz, 100 Hz-1 MHz, or 1 kHz-100 kHz.

Figure 9:
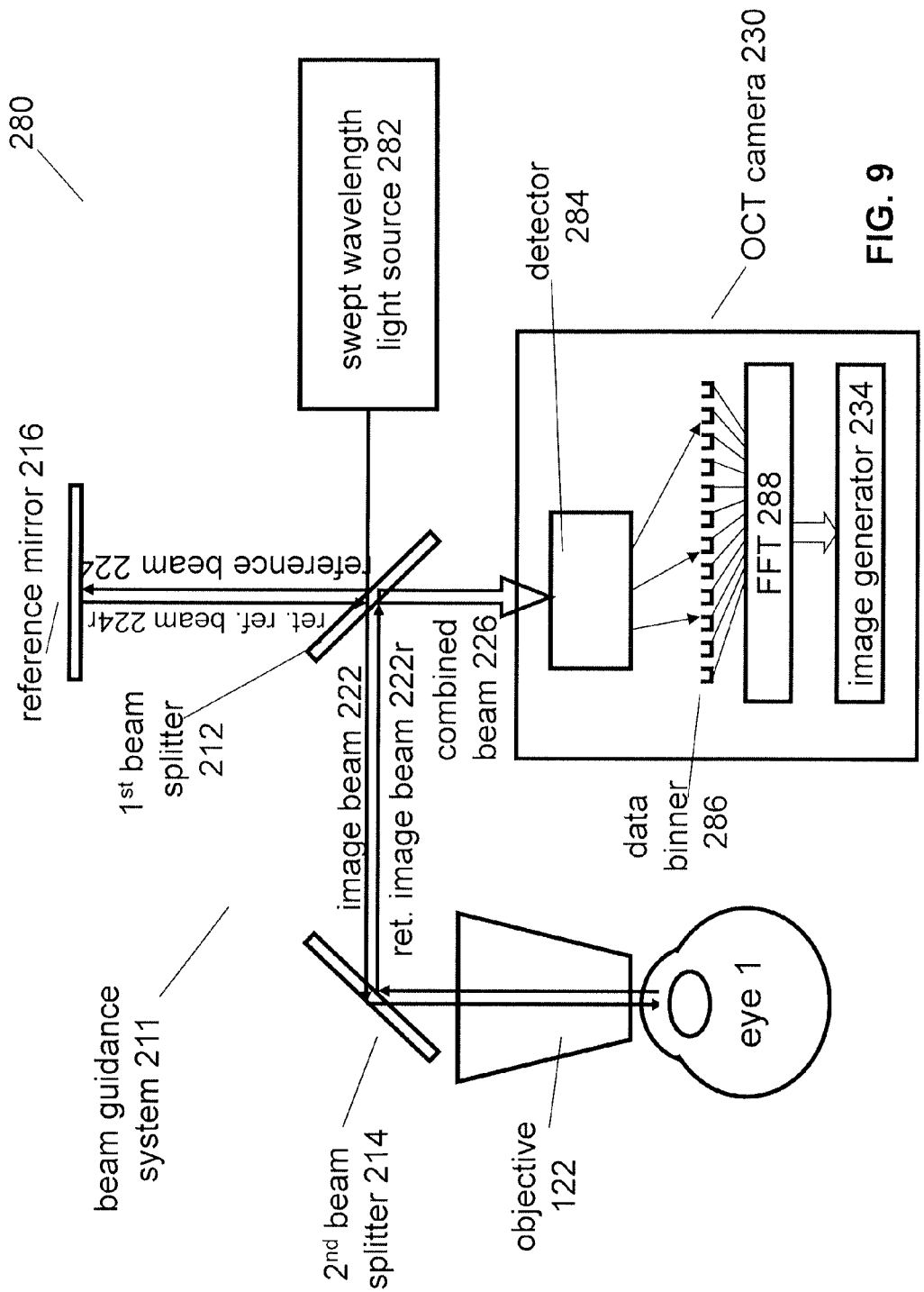
FIG. 9 illustrates an embodiment of a Swept Source Optical Coherence Tomographic imaging system.

FIG. 9 illustrates that some cataract surgical laser systems 100 can include another type of imaging system: a Swept-Source-OCT (SS-OCT) imaging system 280. The SS-OCT imaging system 280 can include a swept wavelength light source 282 that emits a coherent image beam with a narrower bandwidth $W_{source}$, than the SD-OCT light source 210. By advanced modulation techniques the SS-OCT light source 282 can vary the wavelength of the emitted image beam 222, "sweeping" the wavelength λ across the bandwidth $W_{source}$ in time. The SS-OCT imaging system 280 can employ a beam guidance system 211 that is analogous to that of the SD-OCT imaging system 200. In particular, the $1^{st}$ beam splitter 212 can again create the combined beam 226 that carries the imaging information associated with different wavelengths.

As a difference from the spectrometer-based imaging systems, the SS-OCT imaging system 280 separates the different wavelengths or spectral components in time, whereas the SD-OCT systems 200 separate them in space. The different wavelength components, carrying image data corresponding to different z-depths, are separated into a time sequence as the wavelength λ is swept by the SS-OCT light source 282. Therefore, the OCT camera 230 of the SS-OCT systems 280 is different as well.

In some implementations, it consists of a single detector 284 that can detect and resolve the combined beam 226 in very short time intervals. In some embodiments, the detector 284 can be an avalanche photo-diode or a photomultiplier tube. The detector 284 can be capable of transferring or dumping the detected signals, corresponding to different wavelengths or spectral components, to a set of data binners 286. Some embodiments of the SS-OCT imaging system 280 are analogous to the SB-OCT imaging systems because both of them generate the images via spectral decomposition. The spectral components of the SS-OCT image can be assembled into the OCT image similarly as in the SB-OCT systems: a Fast Fourier Transformer 288 can perform a Fourier transformation of the contents of the data binners 286 to assist the image generator 234 to generate the OCT image. The FFT unit 288 can be analogous to the FFT unit 233 in the SD-OCT imaging system 200.

According to the above description, the SS-OCT imaging systems 280 have features similar to the TD-OCT imaging systems as at one phase the imaging data is captured sequentially, not in parallel. However, unlike in TD-OCT systems, the different z-depth imaging data are captured with different spectral components of the combined beam 226, necessitating the performing of the Fourier transformation by the ITT unit 288. In this sense, the SS-OCT imaging systems 280 are related to the SD-OCT imaging systems 200 that manifestly work with different spectral components. SS-OCT systems are close to the SD-OCT systems in one more sense: they sweep the wavelength of the image beam of the swept wavelength light source 282 without moving mechanical parts such as the reference mirror 216. Finally, as the sweeping of the wavelength of the swept wavelength light source 282 can be performed with a speed much above the scanning speed of TD-OCT system as no moving parts are involved in the sweeping, SS-OCT systems 280 can image at speeds much faster than TD-OCT systems, albeit below the imaging speeds of the SD-OCT systems. Therefore, implementations of the SS-OCT imaging system 280 can also be able to generate their images at live refresh rates with acceptable resolution, providing a very useful functionality and actionable feedback for the cataract surgical system 100.

Figure 10:
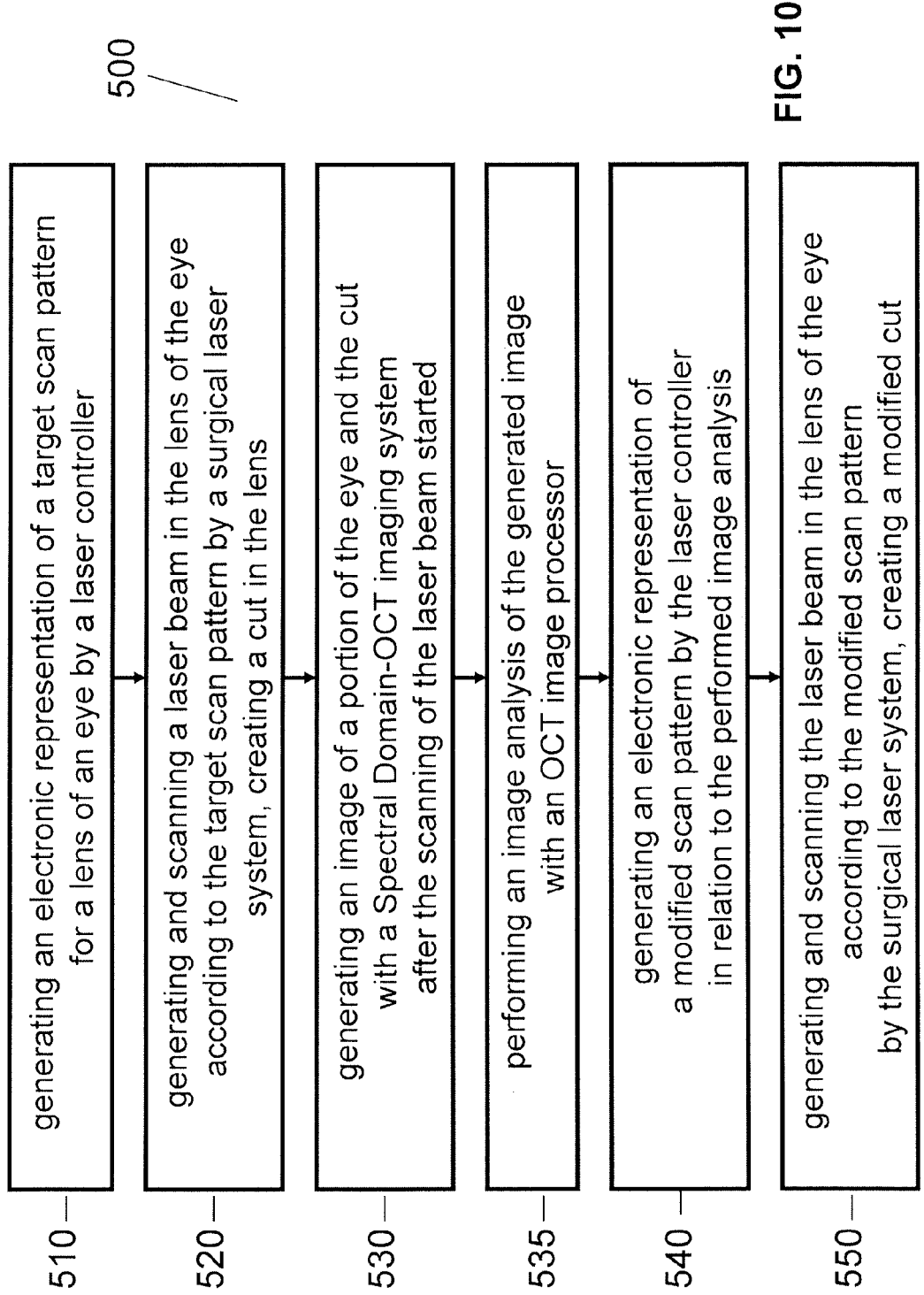
FIG. 10 illustrates an imaging-aided cataract surgical method.

FIG. 10 illustrates an ophthalmic surgical method 500 to operate the cataract surgical system 100. The method 500 can include: a generating an electronic representation of a target scan pattern 302 for the lens 5 of the eye 1 by the laser controller 130 (510); a generating and scanning a surgical laser beam 304 in the lens 5 of the eye according to the target scan pattern 302 by the cataract surgical laser system 100, creating a cut 306 in the lens (520); a generating an image of a portion of the eye and the cut 306 with a Spectral Domain Optical Coherence Tomographic imaging system 200 after the scanning of the laser beam started (530); a performing an image analysis of the generated image with an OCT image processor (535); a generating an electronic representation of a modified scan pattern 312 by the laser controller 130 in relation to the performed image analysis (540); and a generating and scanning the surgical laser beam 304 in the lens 5 of the eye according to the modified scan pattern 312 by the cataract surgical laser system 100, creating a modified cut 314 (550).

In some implementations, the generating an electronic representation of a modified scan pattern 540 can include receiving a modification input from a system operator in response to the generated image of the portion of the eye.

In other implementations, the generating an electronic representation of a modified scan pattern 540 can include analyzing the generated image by the OCT image processor 201; determining a deviation of the cut 306 relative to the target scan pattern 302; and generating a control signal by the OCT image processor 201 for the laser controller 130 to generate the modified scan pattern 312.

FIG. 11 illustrates a related method of cataract surgery 600. The method 600 can include controlling a scanning of the surgical laser beam 304 in the lens 5 of the eye 1 by the laser controller 130 (610); generating images of a portion of the lens 5 at a rate of at least 5 frames per second by the Spectral Domain Optical Coherence Tomographic imaging system 200 (620); performing an analysis of the generated images by an OCT image processor (625); and modifying the scanning of the surgical laser beam 304 by the laser controller 130 in response to the analysis performed by the OCT image processor (630).

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

What is claimed is:

1. A cataract surgical system, comprising:
a laser source, configured to generate a first set of laser pulses;
a guiding optic, coupled to the laser source, configured to guide the first set of laser pulses to a cataract target region in an eye;
a laser controller, configured
to generate an electronic representation of a target scan pattern, and
to control the guiding optic to scan the first set of laser pulses according to a portion of the target scan pattern to create a first photo-disrupted region in the cataract target region;
a Spectral Domain Optical Coherence Tomographic (SD-OCT) imaging system, configured to generate an image that includes a portion of the first photo-disrupted region with an image resolution in the range of 0.5-5 million image points per image and a frame-rate in the range of 20-200 frames/sec; and
an OCT image processor, configured to perform an image analysis of the image, wherein
the laser controller is configured
to generate an electronic representation of a modified scan pattern in relation to the image analysis performed by the OCT image processor, and
to control the guiding optic to scan a second set of laser pulses according the modified scan pattern to create a second photo-disrupted region.

2. The cataract surgical system of claim 1, wherein:
the cataract target region comprises an anterior capsular layer; and
the target scan pattern comprises a set of target points on a cylinder to form at least one of a circular capsulotomy, an anterior capsulotomy, and a curvilinear capsulotomy.

3. The cataract surgical system of claim 1, wherein:
the cataract target region comprises a portion of the lens; and
the target scan pattern comprises a set of target points on at least one of radial chop planes, cylinders, a spiral pattern and a mesh pattern to induce at least one of a chop, a photo-disruption and a lysis of the lens.

4. The cataract surgical system of claim 1, wherein:
the SD-OCT imaging system is configured to have a z-imaging range greater than 4 MM.

5. The cataract surgical system of claim 1, wherein:
the SD-OCT imaging system is configured to have a z-imaging range greater than 6 MM.

6. The cataract surgical system of claim 1, wherein:
the SD-OCT imaging system is configured to generate the image in an imaging time less than 0.1 sec.

7. The cataract surgical system of claim 1, wherein:
the SD-OCT imaging system is configured to generate repeated images with an (x,y) resolution in the range of 500-2,000 A-scans per B-scan.

8. The cataract surgical system of claim 1, wherein:
the OCT image processor is configured to display a feedback for a system operator based on the performed image analysis.

9. The cataract surgical system of claim 8, wherein:
the OCT image processor is configured
to determine a recommended modification input based on the performed image analysis, and
to display the recommended modification input for the system operator.

10. The cataract surgical system of claim 8, wherein:
the OCT image processor is configured
to determine a difference between a reference image taken before the first set of laser pulses were generated and an image taken after the first set of laser pulses generated the first photo-disrupted region; and
to display an indication of the determined difference.

11. The cataract surgical laser system of claim 1, wherein:
the OCT image processor is configured to generate a control signal based on the performed image analysis to cause the laser controller to generate the electronic representation of the modified scan pattern.

12. The cataract surgical laser system of claim 11, wherein:
the OCT image processor is configured to determine a deviation of at least one of a location, an orientation and a shape of the first photo-disrupted region relative to the target scan pattern; and
the laser controller is configured to generate the electronic representation of the modified scan pattern to reduce the determined deviation.

13. The cataract surgical system of claim 11, wherein:
the OCT image processor is configured to determine whether the first photo-disrupted region extends into a region of risk; and
the laser controller is configured to generate the electronic representation of the modified scan pattern to scan the second set of laser pulses outside of the region of risk.

14. The cataract surgical system of claim 11, wherein:
the OCT image processor and the laser controller are integrated.

15. The cataract surgical system of claim 11, wherein:
the OCT image processor is configured to recognize a surgical byproduct; and
the laser controller is configured to generate the electronic representation of the modified scan pattern so that the modified scan pattern is non-overlapping with the surgical byproduct.

16. The cataract surgical system of claim 15, wherein:
the target scan pattern is a chop pattern;
the OCT image processor is configured to recognize a gas bubble as the surgical byproduct; and
the laser controller is configured to generate an electronic representation of a rotated chop pattern as the modified scan pattern such that the rotated chop pattern is non-overlapping with the gas bubble.

17. The cataract surgical system of claim 11, wherein:
the OCT image processor is configured to identify a portion of the first photo-disrupted region where a photo-disruption efficiency was limited; and the laser controller is configured to generate the electronic representation of the modified scan pattern to rescan part of the identified portion.

18. The cataract surgical system of claim 11, wherein:
the OCT image processor is configured
   to analyze a portion of the image that is distinct from the first photo-disrupted region, and
   to generate a feedback based on this analysis.

19. The cataract surgical system of claim 1, wherein:
the SD-OCT imaging system includes a Spectrometer-Based-OCT imaging system, comprising:
a broad-band light source to generate a broad-band beam;
a beam guidance system
   to split the broad-band beam into an image beam and a reference beam,
   to guide the image beam to the eye and to guide a returned image beam from the eye,
   to guide the reference beam to a reference mirror and to guide a returned reference beam from the reference mirror, and
   to combine the returned image beam and the returned reference beam into a combined beam; and
an OCT camera, configured to receive the combined beam, comprising
   a spectral decomposer to decompose the combined beam into spectral components;
   a sensor array to sense the spectral components;
   a Fast-Fourier-Transformer system to generate a Fourier transform from the sensed spectral components; and
   an image generator, to generate an image from the Fourier transformed spectral components.

20. The cataract surgical system of claim 19, the SD-OCT imaging system comprising:
a dedicated Input-Output board configured to output target scan pattern control signals, wherein
the dedicated Input-Output board comprises
   a dedicated memory controller
   a data buffer; and
   an output Digital-Analog Converter; and
the imaging by the SD-OCT imaging system is synchronized with the outputting of the target scan pattern control signals by the output Digital-Analog Converter.

21. A cataract surgical system, comprising:
a laser source, configured to generate a first set of laser pulses;
a guiding optic, coupled to the laser source, configured to guide the first set of laser pulses to a lens of an eye;
a laser controller, configured
   to generate an electronic representation of a target scan pattern, and
   to control the guiding optic to scan the first set of laser pulses according to the target scan pattern to create a first photo-disrupted region;
a Swept-Source Optical Coherence Tomographic (SS-OCT) imaging system, configured to generate an image of a portion of the first photo-disrupted region with an image resolution in the range of 0.5-5 million image points per image and a frame-rate in the range of 20-200 frames/sec; and an OCT image processor, configured to perform an image analysis of the image, wherein
the laser controller is configured
to generate an electronic representation of a modified scan pattern in relation to the image analysis performed by the OCT image processor, and
   to control the guiding optic to scan a second set of laser pulses according the modified scan pattern to create a second photo-disrupted region.

22. The cataract surgical system of claim 21, the Swept-Source-OCT imaging system comprising:
a swept wavelength light source to generate a swept-wavelength beam;
a beam guidance system, configured
   to split the swept-wavelength beam into an image beam and a reference beam,
   to guide the image beam to the eye and to guide a returned image beam from the eye,
   to guide the reference beam to a reference mirror and to guide a returned reference beam from the reference mirror, and
   to combine the returned image beam and the returned reference beam into a combined beam; and
an OCT camera, configured to receive the combined beam, comprising
   a detector to detect the combined beam;
   a data binner to detect the combined beam as a time sequence of data;
   a Fast-Fourier-Transform-system to Fourier transform the detected time sequence of data; and
   an image generator to generate an image from the Fourier transform.

23. A cataract surgical system, comprising:
a surgical laser system, configured
   to generate a surgical laser beam, and
   to scan the surgical laser beam in a cataract target region;
a Spectral Domain Optical Coherence Tomographic (SD-OCT) imaging system, configured to generate an image of a portion of the cataract target region with an image resolution in the range of 0.5-5 million image points per image and a frame-rate in the range of 20-200 frames/sec; and
an OCT image processor, configured
   to perform an image analysis of the image,
   to recognize a surgically undesirable feature in the image, and
   to generate a control signal to stop the scanning of the surgical laser beam.

24. The cataract surgical system of claim 23, wherein:
the surgically undesirable feature comprises at least one of
   a deviation of at least one of a location, an orientation and a shape of a photo-disrupted region relative to a target scan pattern, a surgical byproduct, a bubble, a misplaced cut, a miscalibrated cut, a photo-disruption in a high-risk region, and a limited-efficiency photo-disruption region.

* * * * *